(12) United States Patent
Mérat

(10) Patent No.: US 10,772,875 B2
(45) Date of Patent: Sep. 15, 2020

(54) AGENTS ENHANCING HUR/ELAV PROTEIN LEVELS FOR USE IN THE TREATMENT OF BRAF-MUTATED CANCERS

(71) Applicant: LES HOPITAUX UNIVERSITAIRES DE GENEVE, Geneva (CH)

(72) Inventor: Rastine Mérat, Duingt (FR)

(73) Assignee: LES HOPITAUX UNIVERSITAIRES DE GENEVE, Geneva (CH)

( * ) Notice: Subject to any disclaimer, the term of this patent is extended or adjusted under 35 U.S.C. 154(b) by 0 days.

(21) Appl. No.: 16/493,893

(22) PCT Filed: Mar. 14, 2018

(86) PCT No.: PCT/EP2018/056315
§ 371 (c)(1),
(2) Date: Sep. 13, 2019

(87) PCT Pub. No.: WO2018/167107
PCT Pub. Date: Sep. 20, 2018

(65) Prior Publication Data
US 2020/0085799 A1    Mar. 19, 2020

(30) Foreign Application Priority Data
Mar. 15, 2017    (EP) .................................... 17161090

(51) Int. Cl.
| | | |
|---|---|---|
| A61K 31/435 | (2006.01) | |
| A61K 33/14 | (2006.01) | |
| A61K 31/437 | (2006.01) | |
| A61P 35/00 | (2006.01) | |
| A61K 33/00 | (2006.01) | |
| G01N 33/50 | (2006.01) | |
| A61K 31/4439 | (2006.01) | |
| A61K 31/506 | (2006.01) | |

(52) U.S. Cl.
CPC ............ *A61K 31/437* (2013.01); *A61K 33/00* (2013.01); *A61P 35/00* (2018.01); *G01N 33/5011* (2013.01); *A61K 31/4439* (2013.01); *A61K 31/506* (2013.01)

(58) Field of Classification Search
CPC .............................. A61K 31/435; A61K 33/14
USPC ........................................... 424/722; 514/300
See application file for complete search history.

(56) References Cited

FOREIGN PATENT DOCUMENTS

WO    WO 2013/074594    5/2013

OTHER PUBLICATIONS

Abdelmohsen, K. et al. "Post-transcriptional regulation of cancer traits by HuR" *Wiley Interdiscip Rev RNA*, 2010, pp. 1-24, vol. 1, No. 2.

Blackburn, J. S. et al. "Zebrafish as a model to assess cancer heterogeneity, progression and relapse" *Disease Models & Mechanisms*, 2014, pp. 755-762, vol. 7.

Bollag, G. et al. "Vemurafenib: the first drug approved for BRAF-mutant cancer" *Nature Reviews Drug Discovery*, Nov. 2012, pp. 873-886, vol. 11.

Boussemart, L. et al. "eIF4F is a nexus of resistance to anti-BRAF and anti-MEK cancer therapies" *Nature*, Sep. 4, 2014, pp. 105-109, vol. 513, Supplemental pp. 1-12.

Chen, L. et al. "HIV Protease Inhibitor Lopinavir-induced TNF-a and IL-6 Expression is Coupled to the Unfolded Protein Response and ERK Signaling Pathways in Macrophages" *Biochem Pharmacol.*, Jul. 1, 2009, pp. 1-20, vol. 78, No. 1.

Cho, S.-J. et al. "The RNA-binding Protein RNPC1 Stabilizes the mRNA Encoding the RNA-binding Protein HuR and Cooperates with HuR to Suppress Cell Proliferation" *The Journal of Biological Chemistry*, Apr. 27, 2012, pp. 14535-14544, vol. 287, No. 18.

Cui, Q. et al. "A map of human cancer signaling" *Molecular Systems Biology*, 2007, pp. 1-13, vol. 3, No. 152.

Davies, H. et al. "Mutations of the BRAF gene in human cancer" *Nature*, Jun. 27, 2002, pp. 949-954, vol. 417.

Di Palma, S. et al. "Unraveling cell populations in tumors by single-cell mass cytometry" *Current Opinion in Biotechnology*, 2015, pp. 122-129, vol. 31.

Fienberg, H. G. et al. "Mass Cytometry to Decipher the Mechanism of Nongenetic Drug Resistance in Cancer" *Curr Top Microbiol Immunol*, 2014, pp. 1-11, vol. 377.

Fienberg, H. G. et al. "A Platinum-Based Covalent Viability Reagent for Single-Cell Mass Cytometry" *Cytometry*, 2012, pp. 467-475, vol. 81A.

Gatenby, R. A. et al. "Application of Information Theory and Extreme Physical Information to Carcinogenesis" *Cancer Research*, Jul. 1, 2002, pp. 3675-3684, vol. 62.

Giammanco, A. et al. "Intestinal Epithelial HuR Modulates Distinct Pathways of Proliferation and Apoptosis and Attenuates Small Intestinal and Colonic Tumor Development" *Cancer Res.*, Sep. 15, 2014, pp. 5322-5335, vol. 74, No. 18.

Hardy, S. et al. "Construction of Adenovirus Vectors through Cre-lox Recombination" *Journal of Virology*, Mar. 1997, pp. 1842-1849, vol. 71, No. 3.

Hayes, D. N. et al. "Phase II Efficacy and Pharmacogenomic Study of Selumetinib (AZD6244; ARRY-142886) in Iodine-131 Refractory Papillary Thyroid Carcinoma with or without Follicular Elements" *Clin Cancer Res.*, Apr. 1, 2012, pp. 1-19, vol. 18, No. 7.

(Continued)

*Primary Examiner* — Raymond J Henley, III
(74) *Attorney, Agent, or Firm* — Saliwanchik, Lloyd & Eisenschenk

(57) ABSTRACT

The present invention relates to agents enhancing HuR/ELAV levels for use in the treatment of BRAF-mutated cancers and uses thereof. In particular, the invention relates to the use of agents enhancing HuR/ELAV levels in combination with BRAF inhibitors for the treatment of BRAF-mutated cancers, in particular melanoma and to methods for identifying agents useful for potentiating the effects of BRAF inhibitors, when used in combination.

18 Claims, 16 Drawing Sheets

(56) References Cited

OTHER PUBLICATIONS

Holderfield, M. et al. "Targeting RAF kinases for cancer therapy: BRAF-mutated melanoma and beyond" *Nature Reviews*, Jul. 2014, pp. 455-467, vol. 14.

Jokinen, E. et al. "MEK and PI3K inhibition in solid tumors: rationale and evidence to date" *Ther Adv Med Oncol.*, 2015, pp. 170-180, vol. 7, No. 3.

Kim, I. et al. "HuR represses Wnt/β-catenin-mediated transcriptional activity by promoting cytoplasmic localization of β-catenin" *Biochemical and Biophysical Research Communications*, 2015, pp. 65-70, vol. 457.

King., A. J. et al. "Dabrafenib; Preclinical Characterization, Increased Efficacy when Combined with Trametinib, while BRAF/MEK Tool Combination Reduced Skin Lesions" *PLOS One*, Jul. 2013, pp. 1-10, vol. 8, No. 7, e67583.

Kopetz, S. et al. "Phase II Trial of Infusional Fluorouracil, Irinotecan, and Bevacizumab for Metastatic Colorectal Cancer: Efficacy and Circulating Angiogenic Biomarkers Associated With Therapeutic Resistance" *Journal of Clinical Oncology*, Jan. 20, 2010, pp. 453-459, vol. 28, No. 3.

Lafon, I. et al. "Developmental expression of AUF1 and HuR, two c-myc mRNA binding proteins" *Oncogene*, 1998, pp. 3413-3421, vol. 16.

Lebedeva, S. et al. "Transcriptome-wide Analysis of Regulatory Interactions of the RNA-Binding Protein HuR" *Molecular Cell*, Aug. 5, 2011, pp. 340-352, vol. 43.

Mazan-Mamczarz, K. et al. "RNA-binding protein HuR enhances p53 translation in response to ultraviolet light irradiation" *PNAS*, Jul. 8, 2003, pp. 8354-8359, vol. 100, No. 14.

Merat, R. et al. "Drug-induced expression of the RNA-binding protein HuR attenuates the adaptive response to BRAF inhibition in melanoma" *Biochemical and Biophysical Research Communications*, 2019, pp. 181-187.

Nazarian, R. et al. "Melanomas acquire resistance to B-RAF(V600E) inhibition by RTK or N-RAS upregulation" *Nature*, Dec. 16, 2010, pp. 1-11, vol. 468, No. 7326.

Roche, E. et al. "The PPAβ agonist L-165041 promotes VEGF mRNA stabilization in HPV18-harboring HeLa cells through a receptor-independent mechanism" *Cellular Signalling*, 2014, pp. 433-443, vol. 26.

Smalley, K. S.M. "Understanding Melanoma Signaling Networks as the Basis for Molecular Targeted Therapy" *Journal of Investigative Dermatology*, 2010, pp. 28-37, vol. 130.

Smith, M. P. et al. "Inhibiting Drivers of Non-mutational Drug Tolerance Is a Salvage Strategy for Targeted Melanoma Therapy" *Cancer Cell*, Mar. 14, 2016, pp. 270-284, vol. 29.

Søndergaard, J. N. et al. "Differential sensitivity of melanoma cell lines with BRAF$^{V600E}$ mutation to the specific Raf inhibitor PLX4032" *Journal of Translational Medicine*, 2010, pp. 111, vol. 8, No. 39.

Sun, C. et al. "Reversible and adaptive resistance to BRAF(V600E) inhibition in melanoma"*Nature*, Apr. 3, 2014, pp. 118-122, vol. 508, Supplemental pp. 1-8.

Sutterlüty, H. et al. "p45$^{SKP2}$ promotes p27$^{KIP1}$ degradation and induces S phase in quiescent cells" *Nature Cell Biology*, Aug. 1999, pp. 207-214, vol. 1, No. 4.

Tannock, I. F. et al. "Limits to Personalized Cancer Medicine" *The New England Journal of Medicine*, Sep. 29, 2016, pp. 1289-1294, vol. 375, No. 13.

Tejpar, S. et al. "Prognostic and Predictive Biomarkers in Resected Colon Cancer: Current Status and Future Perspectives for Integrating Genomics into Biomarker Discovery" *The Oncologist*, 2010, pp. 390-404, vol. 15.

Tsai, J. et al. "Discovery of a selective inhibitor of oncogenic B-Raf kinase with potent antimelanoma activity" *PNAS*, Feb. 26, 2008, pp. 3041-3046, vol. 105, No. 8.

Van Der Maaten, L. et al. "Visualizing Data using t-SNE" *Journal of Machine Learning Research*, 2008, pp. 2579-2605, No. 9.

Wang, L. et al. "Generalized stochastic profiling of transcriptional regulatory heterogeneities in tissues, tumors, and cultured cells" *Nat Protoc.*, Feb. 2013, pp. 1-35, vol. 8, No. 2.

Wang, W. et al. "HuR regulates cyclin A and cyclin B1 mRNA stability during cell proliferation" *The EMBO Journal*, 2000, pp. 2340-2350, vol. 19, No. 10.

Yiakouvaki, A. et al. "Myeloid cell expression of the RNA-binding protein HuR protects mice from pathologic inflammation and colorectal carcinogenesis" *The Journal of Clinical Investigation*, Jan. 2012, pp. 48-61, vol. 122, No. 1.

Zhang, W. "BRAF inhibitors: the current and the future" *Current Opinion in Pharmacology*, 2015, pp. 68-73, No. 23.

Zou, T. et al. "Polyamine Depletion Increases Cytoplasmic Levels of RNA-binding Protein HuR Leading to Stabilization of Nucleophosmin and p53 mRNAs" *The Journal of Biological Chemistry*, Jul. 14, 2006, pp. 19387-19394, vol. 281, No. 28.

Written Opinion in International Application No. PCT/EP2018/056315, dated Jul. 23, 2018, pp. 1-14.

A1

A2

AGENTS ENHANCING HUR/ELAV PROTEIN LEVELS FOR USE IN THE TREATMENT OF BRAF-MUTATED CANCERS

CROSS-REFERENCE TO RELATED APPLICATION

This application is the U.S. national stage application of International Patent Application No. PCT/EP2018/056315, filed Mar. 14, 2018.

FIELD OF THE INVENTION

The present invention relates to agents useful in the treatment of BRAF-mutated cancers, in particular BRAF-mutated melanoma.

BACKGROUND

RAF kinases have been associated with cancer since their discovery in 1983. The serine/threonine protein kinase BRAF (B-Raf) is an important player in the receptor tyrosine kinase (RTK)-mediated mitogen-activated protein kinase (MAPK) pathway, where it is activated by the RAS small GTPase. BRAF not only activates the MAPK pathway that affects cell growth, proliferation, and differentiation but also affects other key cellular processes, such as cell migration (through RHO small GTPases), apoptosis (through the regulation of BCL-2), and survival (through the HIPPO pathway). The BRAF gene was found constitutively activated by mutation in 15% of all human known cancer types, in particular in melanoma (Davies et al., 2002, *Nature*, 417(6892):949-954). BRAF was reported to be mutated at several sites; however, the vast majority of mutated BRAF are V600E (1799T>A nucleotide change), characterizing up to 80% of all BRAF mutations (Davies et al., 2002, supra). This mutation results in amino acid change that confers constitutive kinase activity. Most of the BRAF mutations result either in the acquirement of new phosphomimetic residues or in the release of the auto-inhibitory conformation imposed by the N-terminal region, which enhances the dimerization of the kinase domain, a crucial process for kinase activity. According to recent studies, BRAF is reported to be mutated in about 8% or all cancers and approximately one half of all melanomas harbor a $BRAF^{T1799A}$ transversion which encores the constitutively active BRAF-V600E oncoprotein (Holderfield et al., 2014, *Nature Reviews*, 14, 455-467). The BRAF V600E mutation is also the most common genetic mutation detected in patients with papillary thyroid cancer (PTC) and occurs in approximately 45% of patients (Davies et al., 2002, supra). Mutations in the BRAF gene are also found in about 10% of colorectal carcinoma (CRC) patients, 6% in lung cancers and nearly all cases of papillary craniopharyngioma, classical hairy-cell leukaemia (HCL-C) and metanephric kidney adenoma (Holderfield et al., 2014, supra) are usually associated with significant poorer prognosis (Tejpar et al., 2010, *Oncologist*, 15(4):390-404).

BRAF inhibitors have been developed by different companies and the most commonly used are vemurafenib (marketed as Zelboraf by Roche) and dabrafenib (marketed as Tafinlar by GSK), but others exist such as LGX818 (encorafenib; Novartis), XL281 (Exelixis), and CEP-32496 (Ambit Biosciences Corporation) (Zhang, 2015, *Curr Opin Pharmacol.*, 23:68-73). Impressive clinical results have shown that targeted therapies for melanoma, i.e. BRAF and MEK inhibitors, can efficiently treat highly mutagenic solid malignancies by blocking critical cell survival pathways. However, subsequent clinical observations have demonstrated that these inhibitors, even when combined, are rarely curative and that resistance almost inevitably develops within a few weeks or months (Tannock et al., 2016, *N Engl J Med*, 375:1289-94). Currently, great efforts are being deployed to understand the mechanisms behind this resistance (Smalley, 2010, *J Invest Dermatol*, 130:28-37), and to develop other combinatory therapies to target the compensatory pathways that become activated in response to pathway inhibition, e.g. the PI(3)K (Phosphatidylinositol-4,5-bisphosphate 3-kinase) pathway (Jokinen et al., 2015, *Ther Adv Med Oncol*, 7: 170-80). Nevertheless, the likelihood of resistance to these new combinations is also high. The somatic evolution of malignant tissues involves dynamic emergent processes including nondeterministic alterations of genetic pathways (Gatenby et al., 2002, *Cancer Res*, 62:3675-84) and non-genetic adaptive responses of malignant cells to their environment and to therapies which affect intra-tumor heterogeneity (Tannock et al., 2016, supra).

Targeted therapy-induced mutations, the resulting genetic heterogeneity and the consequent induced resistance are irreversible processes. Irreversible genetic resistance contrasts with the reversible non-genetic adaptive resistance to these drugs documented in many recent studies (Nazarian et al., 2010, *Nature*, 468:973-7; Sun et al., 2014, *Nature*, 508:118-22; Boussemart et al., 2014, *Nature*, 513:105-9), which occurs in vivo in an undetermined proportion of malignant cells, qualified here as reversible tumor heterogeneity (RTH).

Therefore, tumor plasticity and the heterogeneous response of melanoma cells to targeted therapies are major limits for the long term efficacy of this line of therapy. If BRAF mutated melanoma develop resistance during the course of the BRAF inhibitor therapies, the response of other BRAF-driven cancers to BRAF inhibitors is even more disappointing: only ~5% of BRAF-mutant colorectal patients respond to vemurafenib (Kopetz et al., 2010, *J Clin Oncol.*, suppl: 28), and thyroid cancers do not respond to selumetinib (Hayes et al., 2012, *Clin Cancer Res.*, 18:2056-65).

Targeting tumor plasticity is theoretically possible through the modulation of the expression of RNA-binding proteins which can affect many different and compensatory mechanisms of the adaptive response of malignant cells to targeted therapies within the cancer signaling network (Cui et al., 2007, *Mol Syst Biol*, 3:152).

Human antigen R (HuR) is a modulator of gene expression and a trans-acting factor in the mRNA-processing machinery used in the cell stress response which is mainly considered as a tumorigenic protein, partly because some of its targets are cell cycle- and apoptosis-regulating proteins and partly because its expression pattern increases in some malignancies (Abdelmohsen et al., 2010, *Wiley Interdiscip Rev RNA*, 1:214-29). However, HuR involvement in cancer is highly complex (Cho et al., 2012, *J Biol Chem*, 287: 14535-44) according to the available in vivo experimental data (Yiakouvaki et al., 2012, *J Clin Invest*, 122:48-61; Giammanco et al., 2014, *Cancer Res*, 74:5322-35). Based on various studies HuR, is estimated to have between 5'000 to more than 7'000 direct mRNA targets (Lebedeva et al., 2011, *Mol Cell*, 43:340-52) and within the cancer signaling network (Cui et al., 2007, supra), at least 10% of the nodes, including highly connected ones, belong to the HuR repertoire. Agents capable of modulating nucleo-cytoplasmic expression of the protein HuR/ELAV have been developed, for example for the treatment of metabolic disorders (Roche et al., 2014, *Cellular Signalling*, 26, 433-443) and their effect on the modulation of expression of HuR/ELAV has been described as accessory and not considered as being crucial for their current therapeutic use.

Undoubtedly, there is a need to develop effective treatments for BRAF mutated solid tumor cancers, in particular melanoma that would prevent the development of drug resistance.

SUMMARY OF THE INVENTION

The invention is based on the unexpected findings that, contrary to earlier studies aiming at the decrease of HuR global and cytoplasmic expression of the protein HuR/ELAV for a therapeutic benefit in cancerology (Abdelmohse et al., 2010, *Wiley Interdiscip Rev RNA*, 1(2): 214-29), overexpression of the protein HuR/ELAV, including in the cytoplasm, induces an increased sensitivity of tumor cells to BRAF inhibitors (e.g. vemurafenib). Further, the sensitization effect obtained by enhancers of HuR/ELAV expression is achieved through a decrease of cellular heterogenicity, a blocking of the emergence of cell populations presenting markers of resistance (pERK1/2, pAKT, EGFR, PDGFbR, p4E-BP1) and increased percentage of tumor cells in the cellular cycle phase where increased sensitivity to BRAF inhibitors occurs. Noteworthy, the cell sensitization effect is observed only in presence of a BRAF inhibitor, the overexpression of HuR/ELAV protein having only a slight cytostatic effect, per se. Therefore, the use of enhancers of HuR/ELAV protein levels, in particular enhancers of cellular/cytoplasmic expression, in combination with at least one BRAF inhibitor is believed to be particularly useful for the treatment of BRAF mutated solid tumor cancers, in particular melanomas.

According to one aspect of the invention, is provided an enhancer of HuR/ELAV protein for the treatment of a BRAF-mutated cancer, wherein said enhancer of HuR/ELAV protein is to be administered in combination with a BRAF inhibitor.

According to another aspect of the invention, is provided a use of an enhancer of HuR/ELAV protein for the preparation of a pharmaceutical composition for the treatment of a BRAF-mutated cancer, wherein said enhancer of HuR/ELAV protein is to be administered in combination with at least one BRAF inhibitor.

According to another aspect of the invention, is provided a pharmaceutical composition comprising at least one enhancer of HuR/ELAV protein and at least one BRAF inhibitor and at least one pharmaceutically acceptable carrier.

According to another aspect of the invention, is provided a method for treating a subject who is suffering from a BRAF-mutated cancer, said method comprising the administration of a therapeutically effective amount of at least one enhancer of HuR/ELAV protein or any suitable pharmaceutically acceptable formulation thereof, in a subject in need thereof, wherein said at least one enhancer of HuR/ELAV protein or any suitable pharmaceutically acceptable formulation thereof is to be administered in combination with at least one BRAF inhibitor.

In another embodiment, the invention provides a method of prevention of the emerging of adaptive BRAF therapy resistance comprising the administration of a therapeutically effective amount of at least one enhancer of HuR/ELAV protein or any suitable pharmaceutically acceptable formulation thereof, in a subject suffering from a BRAF mutated solid tumor cancer, wherein said at least one enhancer of HuR/ELAV protein or any suitable pharmaceutically acceptable formulation thereof is to be administered in combination with at least one BRAF inhibitor.

In another embodiment, the invention provides a method of identifying agents useful in the potentiation of therapeutic effects of BRAF inhibitors.

(n=7417); for vemurafenib-treated cells Sp1 (n=5143), Sp2 (n=10485), Sp3 (n=9636), Sp4 (n=2983). A2: Left: viSNE map of the Ki67 marker in aG (m.o.i. 5) DMSO-treated cells (aGnt) (top) compared to vemurafenib-treated cells (aGt) (bottom). Middle: Corresponding SPADE spanning-tree generated from viSNE maps; Right: Corresponding pie-charts of the proportion of each subpopulation within each spanning-tree for DMSO-treated cells Sp1 (n=1721), Sp2 (n=1110), Sp3 (n=3293), Sp4 (n=5707); for vemurafenib-treated cells Sp1 (n=12184), Sp2 (n=10319), Sp3 (n=7152), Sp4 (n=2033)). A3: Left: viSNE map of the Ki67 marker in aH (m.o.i. 5) DMSO-treated cells (aHnt) (top) compared to vemurafenib-treated cells (aHt) (bottom). Middle: Corresponding SPADE spanning-tree generated from viSNE maps; Right: Corresponding pie-charts of the proportion of each subpopulation within each spanning-tree for DMSO-treated cells Sp1 (n=2312), Sp2 (n=2525), Sp3 (n=4897), Sp4 (n=6096); for vemurafenib-treated cells Sp1 (n=425), Sp2 (n=1077), Sp3 (n=5549), Sp4 (n=9170). In A1-A3, SPADE spanning-trees, Ki67 expression was used to select four subpopulations (Sp1, Sp2, Sp3 and Sp4), the size of the dots is proportional to the number of cells. The grey-scale color of the dots indicates the relative Ki67 expression level (based on the median value for each cluster). A1-A3: pie-charts indicate the proportion of each subpopulation within each spanning-tree. B: GFP marker distribution expression in aGnt and aHnt cells as the negative control for indicating the sensitivity of the mass cytometry analysis.

Figure 5:
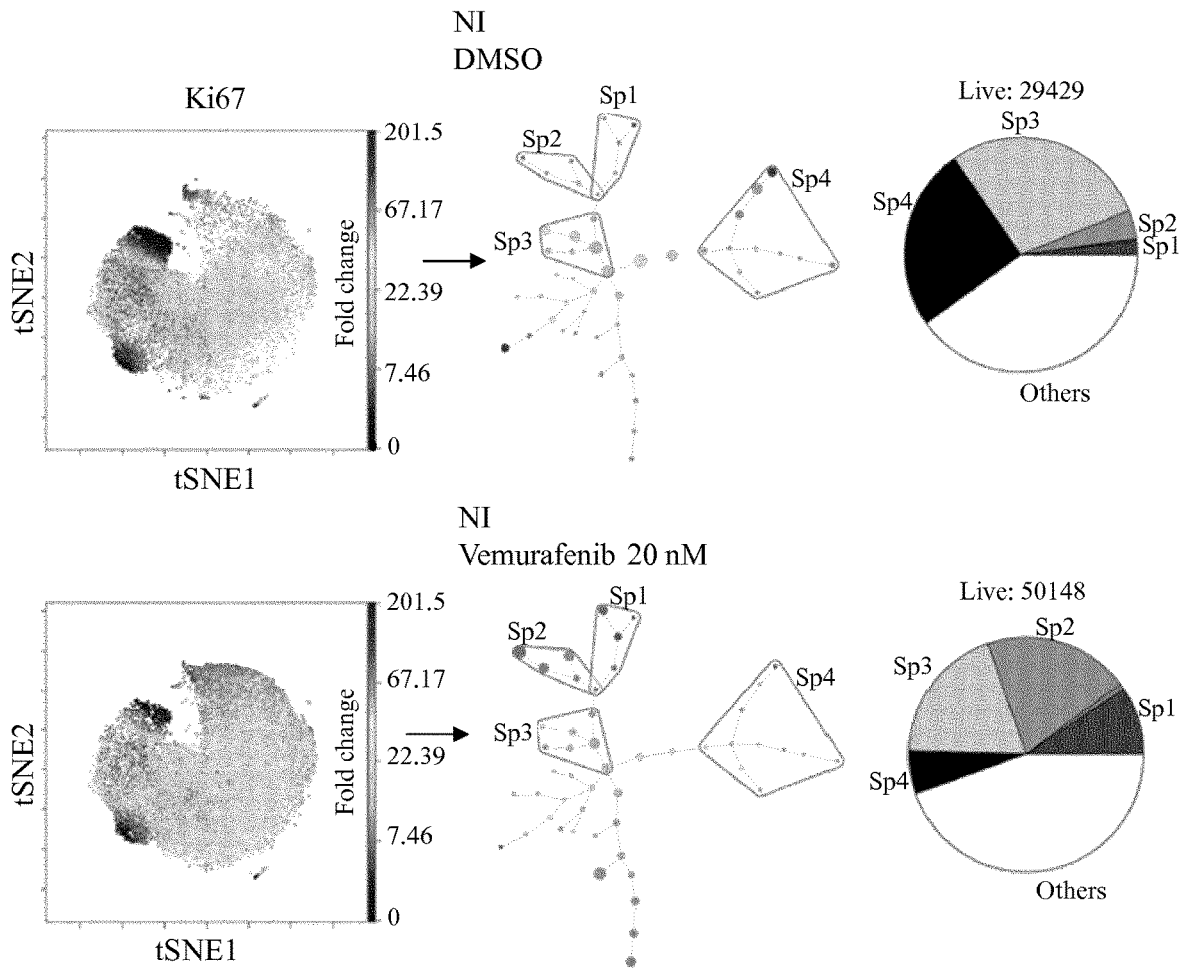
FIG. 5 shows mass cytometry analysis of the low-dose vemurafenib-induced paradoxical proliferation and its suppression in HuR-overexpressing A375 cells in vemurafenib-treated (20 mM) compared to DMSO-treated cells, as described in Example 2. A1: Left: viSNE map of the Ki67 marker in the NI samples in DMSO-treated cells (top) compared to vemurafenib-treated cells (bottom). Middle: Corresponding SPADE spanning-tree generated from viSNE maps; Right: Corresponding pie-charts of the proportion of each subpopulation within each spanning-tree for DMSO-treated cells Sp1 (n=661), Sp2 (n=1218), Sp3 (n=8414), Sp4
Figure 5:
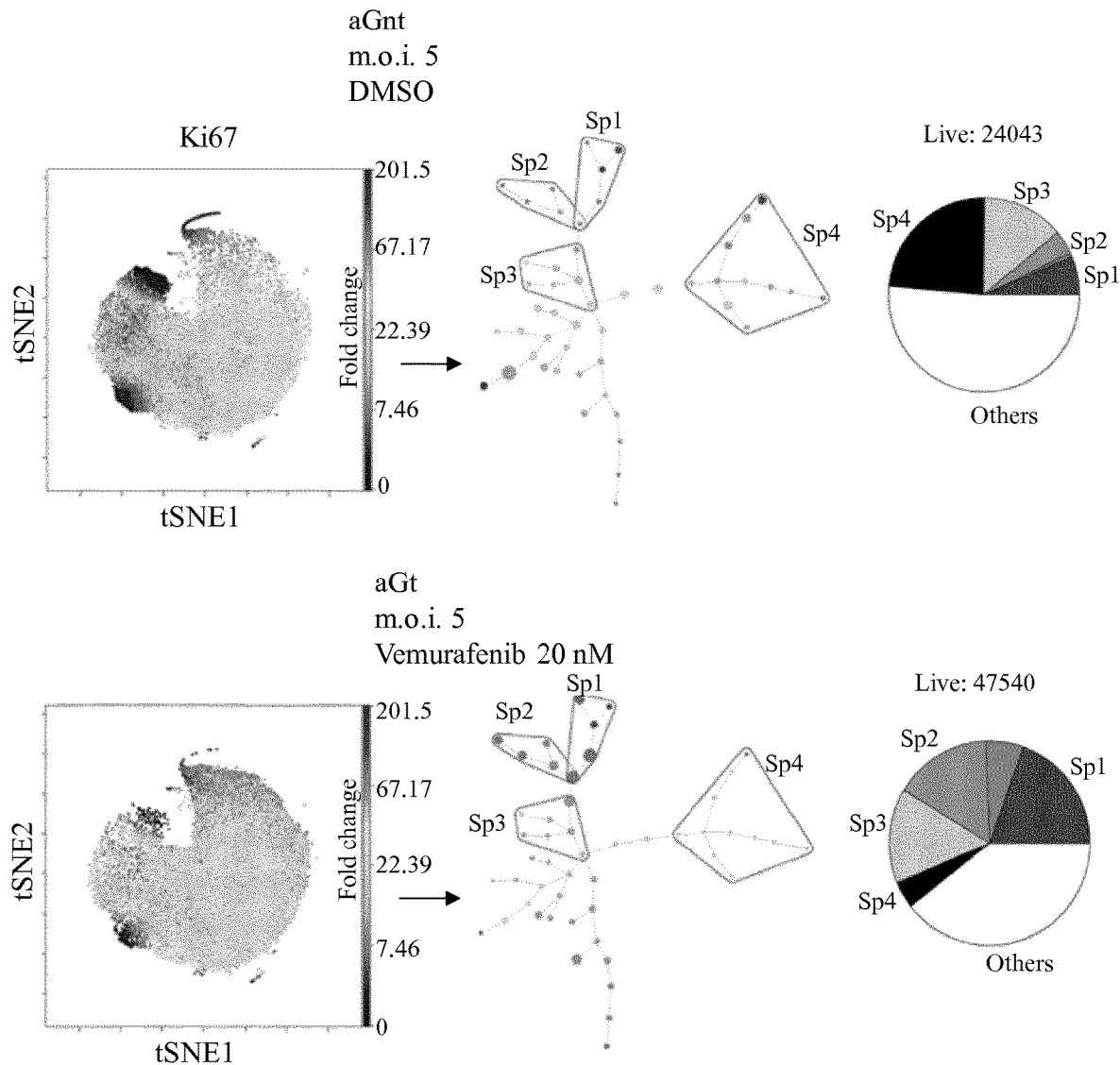
Figure 5:
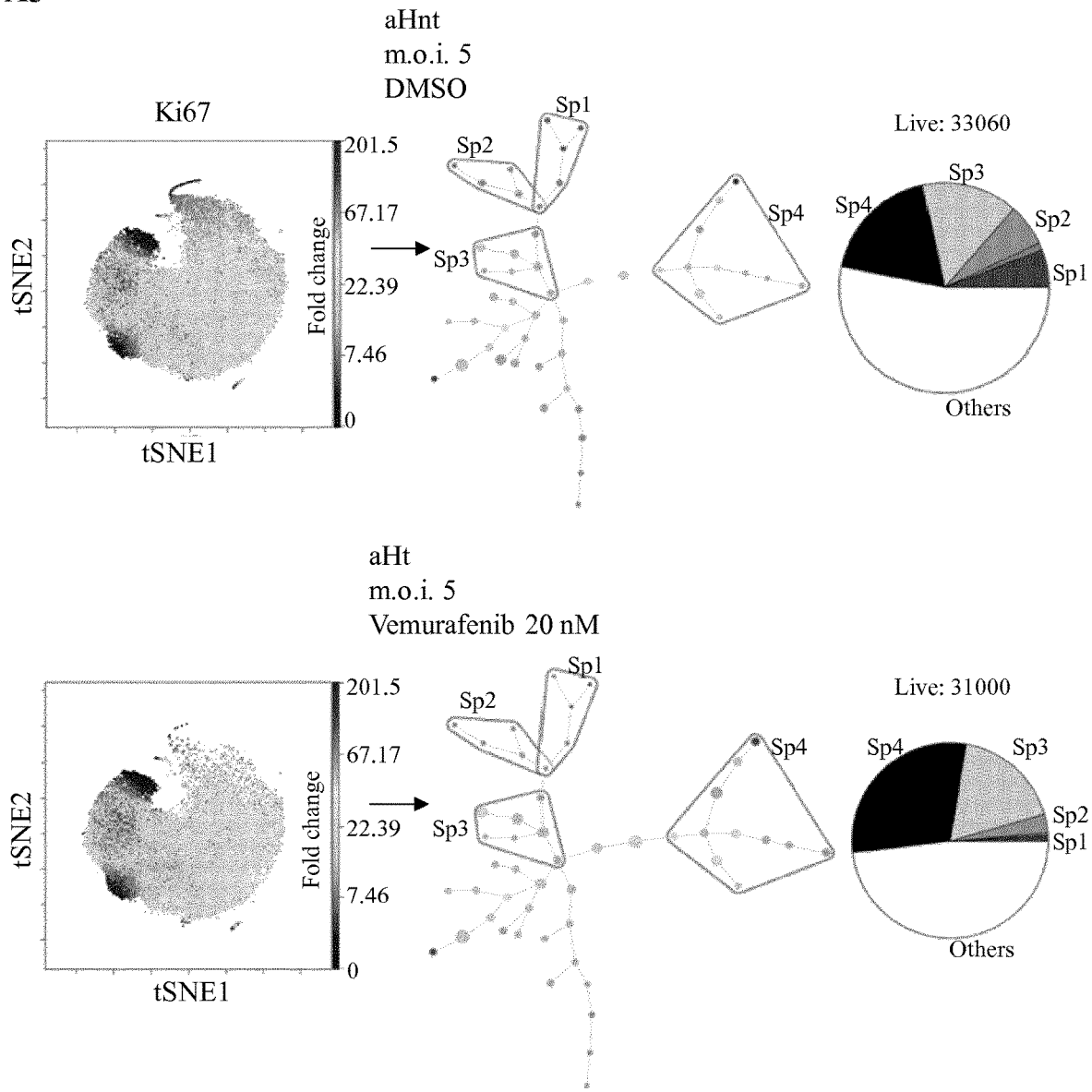
Figure 5:
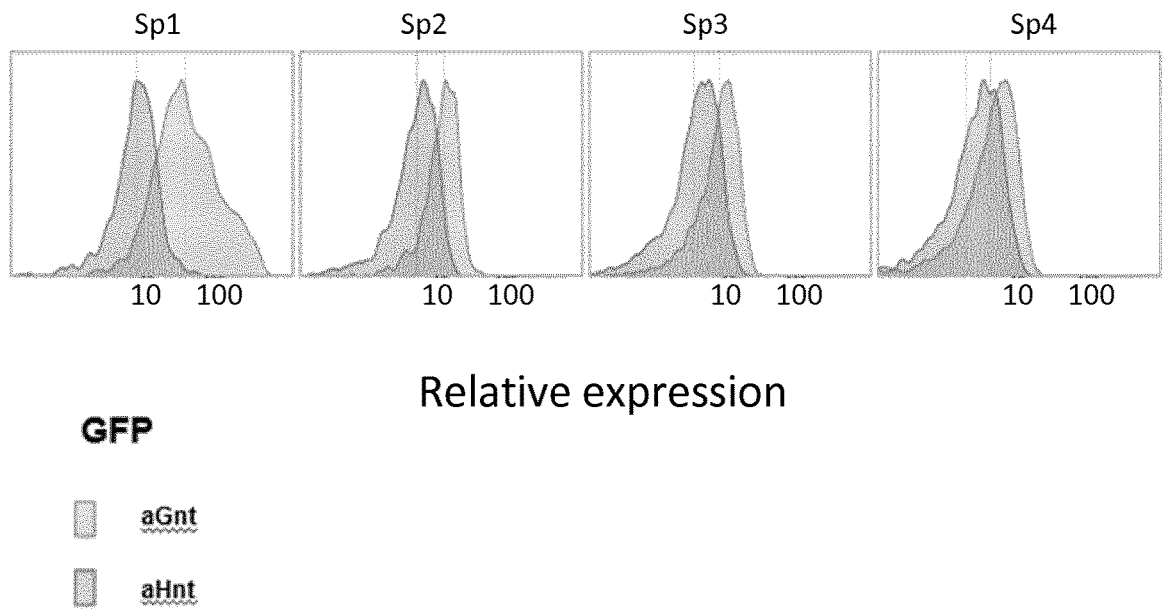
Figure 6:
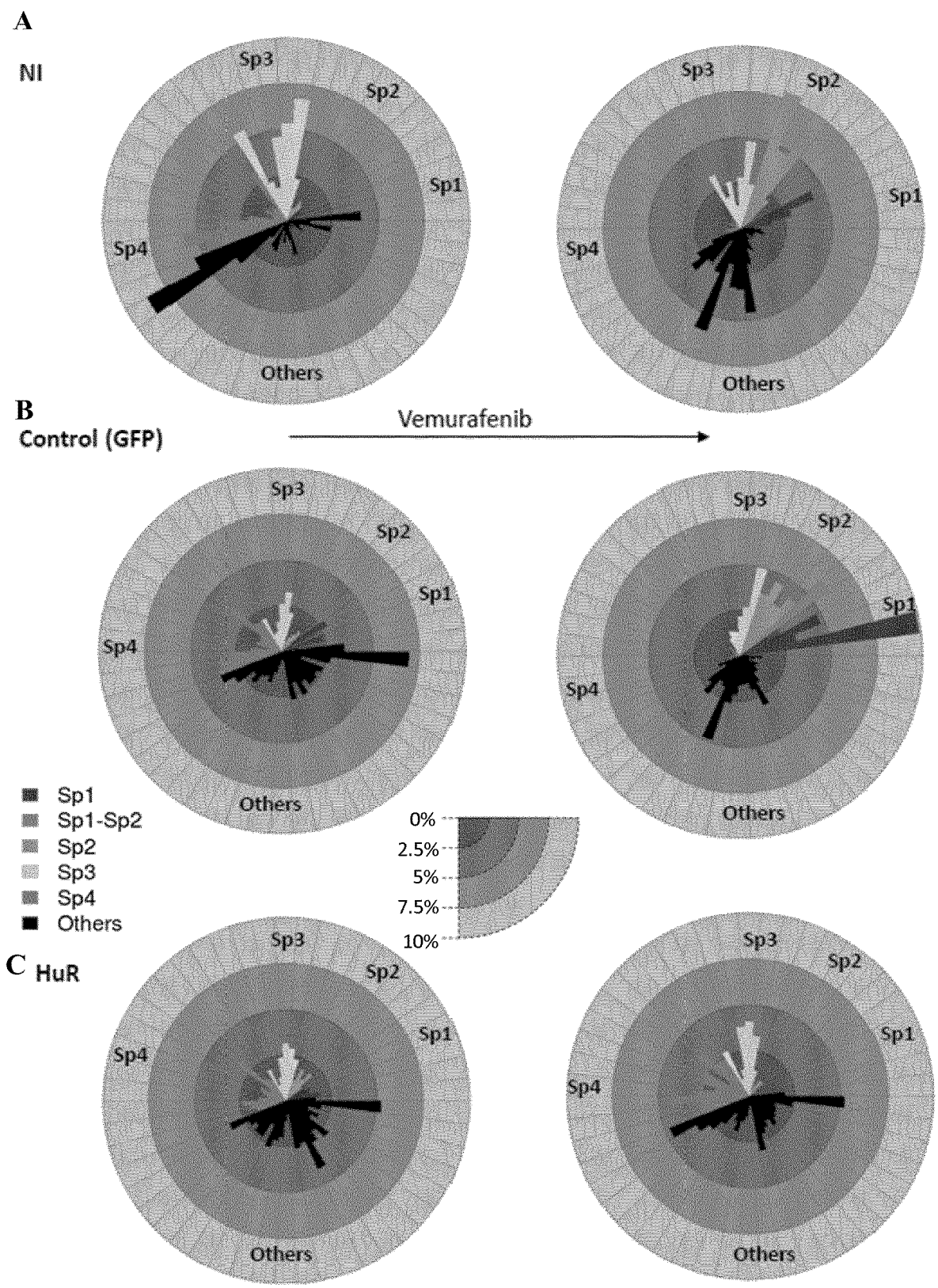
Figure 7A:
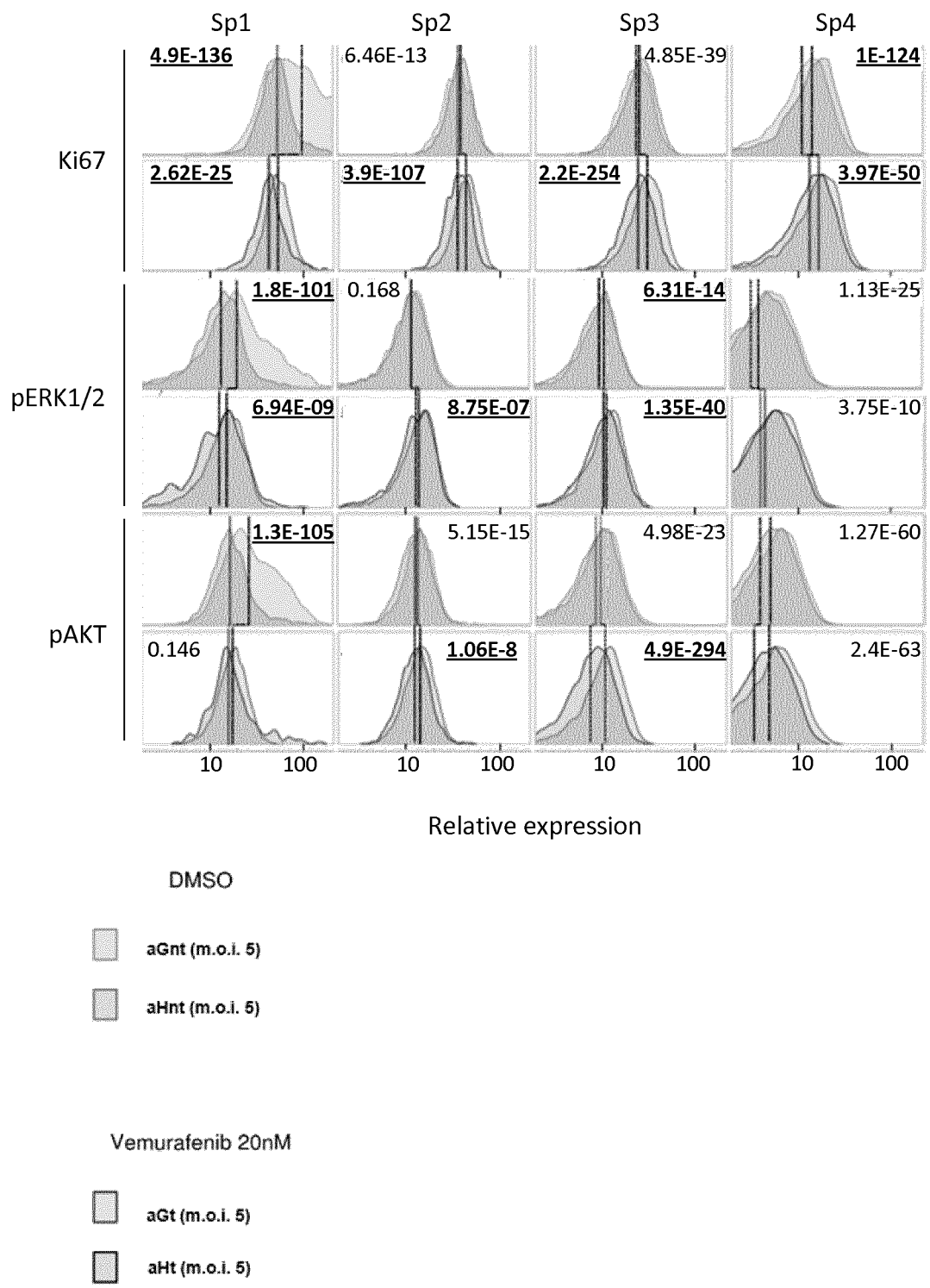
Figure 7A:
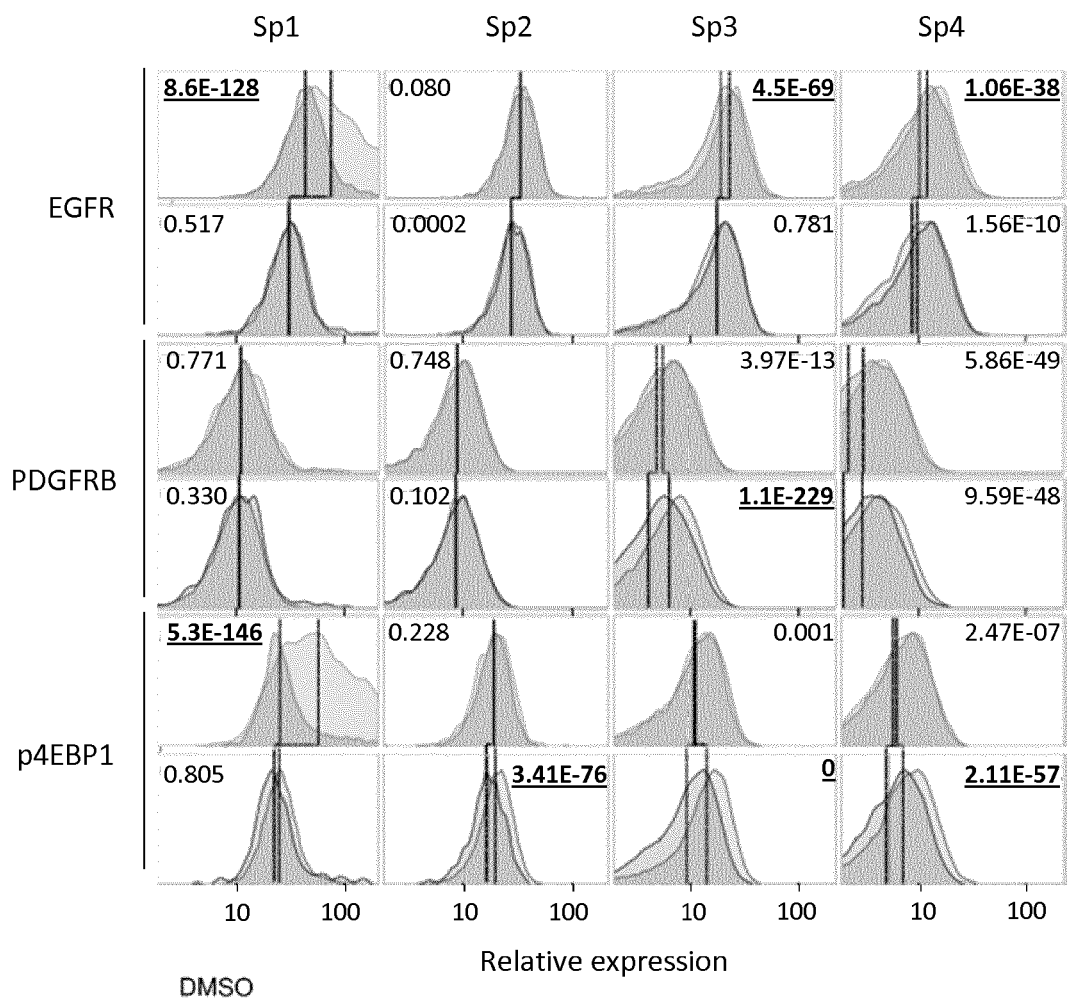
Figure 7A:
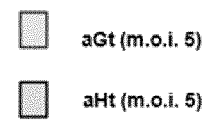
Figure 7B:
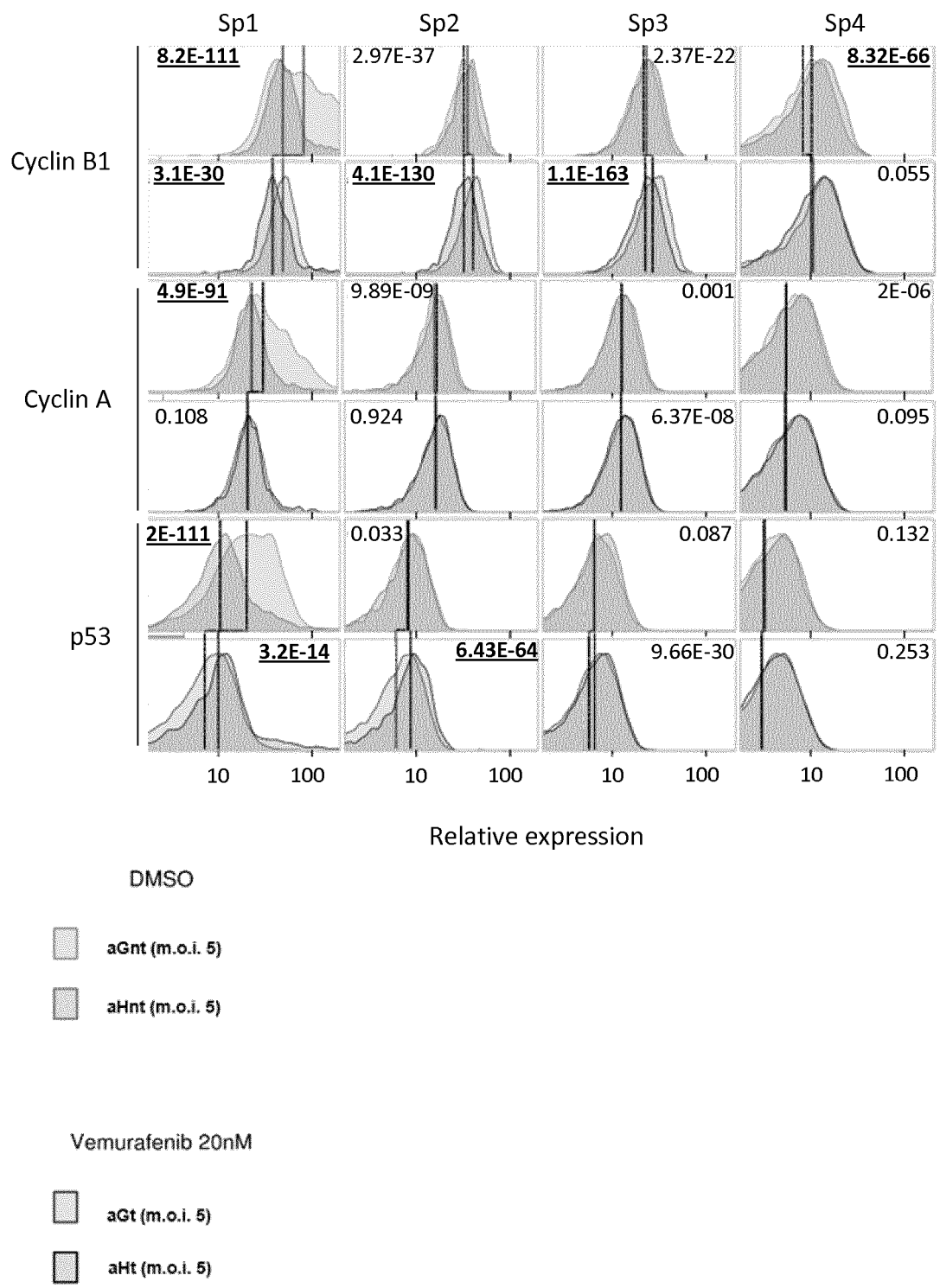
Figure 7B:
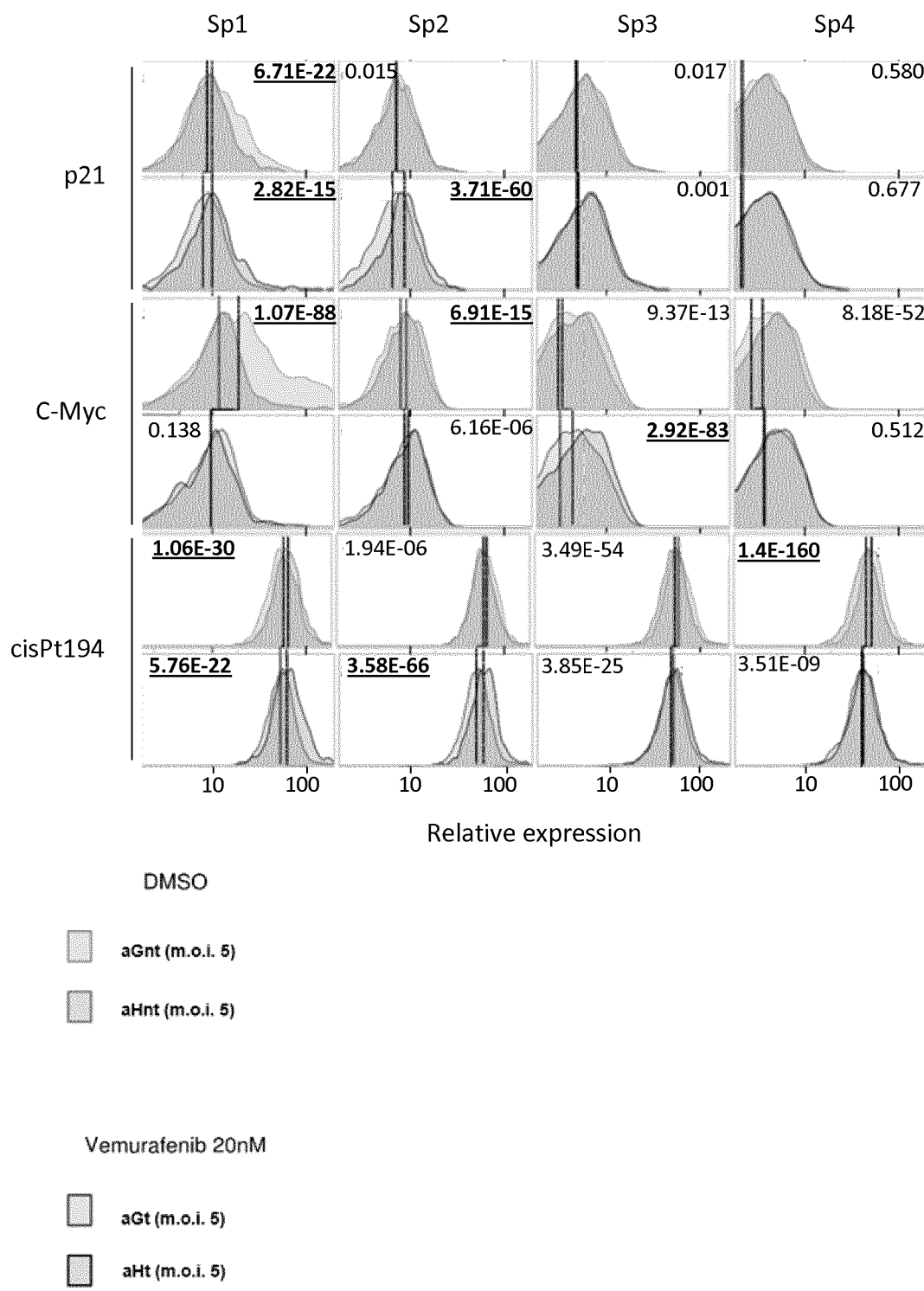

FIG. 6 shows how HuR overexpression affects cell heterogeneity in terms of the proportion of the 50 clusters identified in FIG. 5, as described in Example 2. The clusters belonging to the same subpopulations as defined in FIG. 5 are grouped next to each other and identified by the gray scale color of each subpopulation. Note the disappearance of the most proliferative clusters in the HuR overexpressing sample but not in the NI, neither the control GFP overexpressing samples. A: representation of the cell subpopulations (Sp1, Sp2, Sp3, Sp4) in the NI samples in DMSO-treated cells (left) compared to vemurafenib-treated cells (right). B: representation of the cell subpopulations (Sp1, Sp2, Sp3, Sp4) in aG (m.o.i. 5) DMSO-treated cells (aGnt, control) (left) compared to vemurafenib-treated cells (aGt) (right); B: representation of the cell subpopulations (Sp1, Sp2, Sp3, Sp4) in DMSO-treated cells (aGnt, control) (left) compared to vemurafenib-treated cells (aGt) (right); C: representation of the cell subpopulations (Sp1, Sp2, Sp3, Sp4) in aH (m.o.i. 5) DMSO-treated cells (aHnt) (left) compared to vemurafenib-treated cells (aHt) (right).

FIG. 7 shows comparative analysis by single-mass cytometry of each of the four subpopulations (Sp1, Sp2, Sp3 and Sp4) based on the distribution of the expression levels in the 12 markers used to generate the viSNE maps, as described in Example 3 for aGnt/aHnt cells (top row of each marker, lines for comparisons of median value), aGt/aHt cells (bottom row of each marker, lines for comparisons of median value), aGnt/aGt (bordered histograms, comparison between top and bottom row, for comparison of median values) and aHnt/aHt (bordered histograms, comparison between top and bottom row, line for comparison of median values). The P-values (t-test) for paired comparisons are underlined for differences considered significant.

Figure 8:
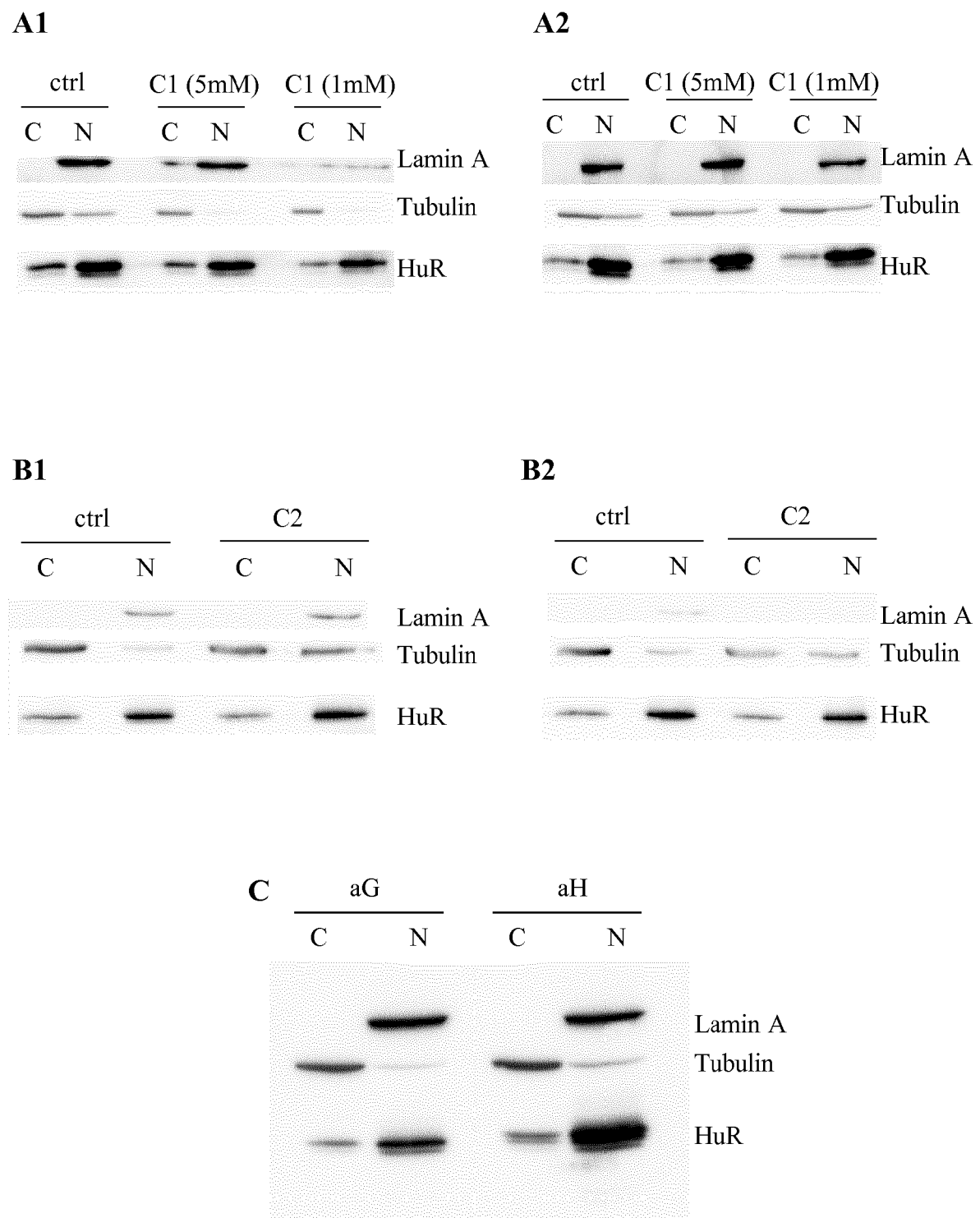

FIG. 8 shows expression level of cytoplasmic (C) and nuclear (N) HuR determined by western-blot analysis as described in Example 5 for a compound of the invention (LiCl) (FIG. 9) compared to comparative compounds not of the invention (eflornithine (FIG. 8A1-A2) and Lopinavir (FIG. 8B1-B2)). $A_{1,2}$: western-blot analysis on C1-treated and control (ctrl) cells ($A_1$-A375 cells; $A_2$-MALME-3M cells) $B_{1,2}$: western-blot analysis on C2 (15 μM)-treated and control (DMSO, ctrl) cells ($B_1$-A375 cells; $B_2$-MALME-3M cells); C: western-blot analysis on cells infected with a control adenovirus (aG) or an adenovirus overexpressing HuR (aH) at m.o.i 125 (shown as a positive control of successful increased HuR nuclear and cytoplasmic expression).

Figure 9:
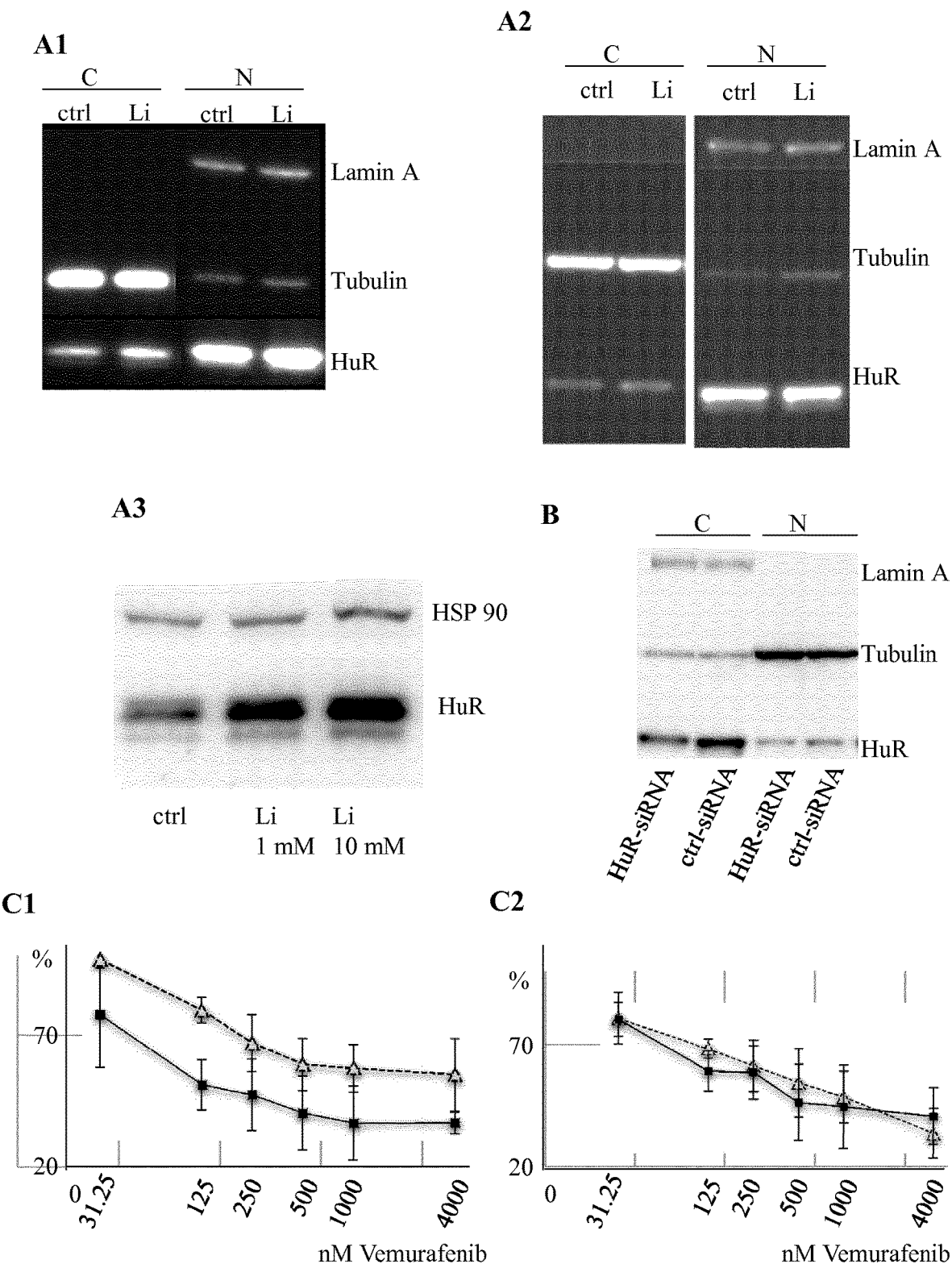

FIG. 9 shows the effect of LiCl on the expression levels of HuR and cell proliferation as described in Example 6. $A_{1,2}$: western-blot analysis on LiCl (1 mM)-treated and control (ctrl) cells ($A_1$-A375 cells; $A_2$-MALME-3M cells); $A_3$: whole cell extract western-blot analysis on HuR-expressing adenovirus-infected A375 melanoma cells: untreated (ctrl) or treated with Li at two concentrations: 1 mM and 10 mM; B: expression level of cytoplasmic (C) and nuclear (N) HuR determined by western-blot analysis in MALME-3M cells transfected with HuR-siRNA or ctrl-siRNA; $C_{1,2}$: proliferation of LiCl and vemurafenib (at increasing dose)-treated (solid line and squares) and control (dotted line and triangles) cells transfected with HuR-siRNA ($C_2$) or ctrl-siRNA ($C_1$).

DETAILED DESCRIPTION

The expression "BRAF inhibitor" defines herewith an agent that inhibits completely or partially the activity of BRAF kinase. These inhibitors are either selective (type 1) or not selective (type 2). Examples of BRAF inhibitors include those as described in *Thèse Lise Boussemart*, 2014, Université Paris XI such as vemurafenib (PLX4032, N-{3-[5-(4-chlorophenyl)-1H-pyrrolo[2,3-b]pyridine-3-carbonyl]-2,4-difluorophenyl}propane-1-sulfonamide):

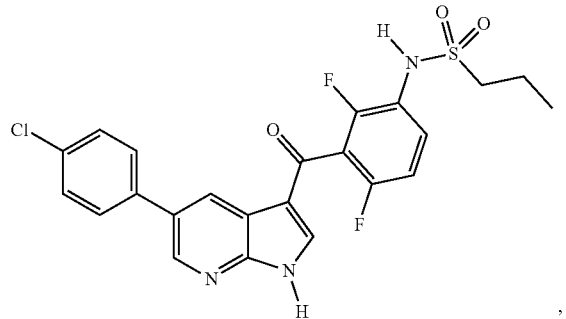 [SMILES: CCCS(=O)(=O)Nc1ccc(F)c(C(=O)c2c[nH]c3ncc(-c4ccc(Cl)cc4)cc23)c1F]

vemurafenib precursor (PLX 4720, N-[3-(5-chloro-1H-pyrrolo[2,3-b]pyridine-3-carbonyl)-2,4-difluorophenyl]propane-1-sulfonamide):

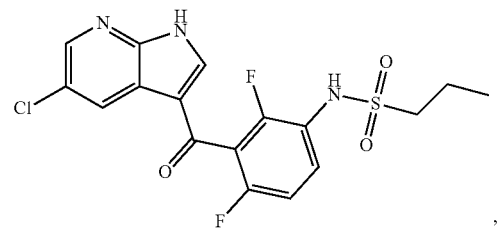 [SMILES: CCCS(=O)(=O)Nc1ccc(F)c(C(=O)c2c[nH]c3ncc(Cl)cc23)c1F]

encorafenib (LGX818, [Methy[(2S)-1-{5-chloro-2-fluoro-3-[(methylsulfonyl)amino]phenyl}-1-isopropyl-1H-pyrazol-4-yl)-2-pyrimidinyl]amino}-2-propanyl]carbamate):

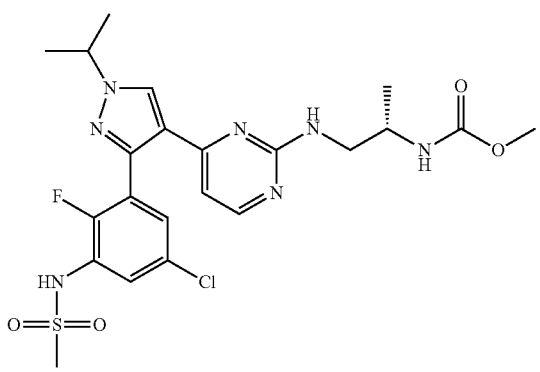

GDC0879 (2-[4-[(1E)-1-(hydroxyimino)-2,3-dihydro-1H-inden-5-yl]-3-(pyridine-4-yl)-1H-pyrazol-1-yl]ethan-1-ol):

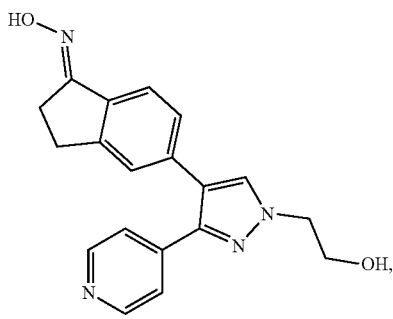 [SMILES: OCCn1cc(-c2ccc3c(c2)CC/C3=N\O)c(-c2ccncc2)n1]

CEP-32496 (1-[3-(6,7-dimethoxyquinazolin-4-yl)oxyphenyl]-3-[5-(1,1,1-trifluoro-2-methylpropan-2-yl)-1,2-oxazol-3-yl]urea):

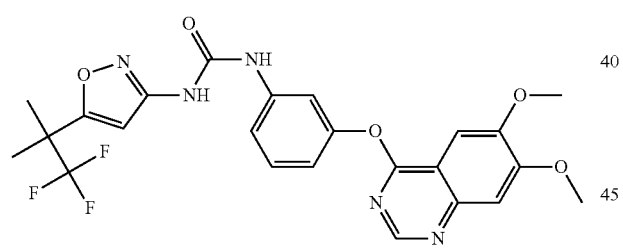

and dabrafenib (N-{3-[5-(2-aminopyrimidin-4-yl)-2-tert-butyl-1,3-thiazol-4-yl]-2-fluorophenyl}-2,6-difluorobenzene-1-sulfonamide):

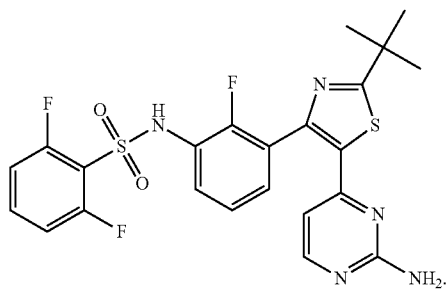 [SMILES: CC(C)(C)c1nc(-c2cccc(NS(=O)(=O)c3c(F)cccc3F)c2F)c(-c2ccnc(N)n2)s1]

Beyond scaffold and structure-based studies used for their discovery (Tsai et al, 2007, *PNAS*, 105:3041-3046; Bollag et al, 2012, *Nature Reviews Drug Discovery*, 11:873-886), the inhibitory potency (to inhibit completely or partially the activity of BRAF kinase) and selectivity of BRAF inhibitors are usually assessed, but not exclusively, with in vitro BRAF kinase assays in which the compound potency ($IC_{50}$) is measured against the kinase activity of various BRAF orthologs and BRAF mutants. For this purpose various assays like for example BRAF/CRAF-activated MEK ATPase coupled assays can be used. These in vitro assays also include usually ATP competition binding assays (ability to displace a known labelled ATP-competitive ligand) and cellular assays (for detection of inhibition of downstream pERK and pMEK activity and possibly inhibition of cell proliferation) (King et al, 2013, *PLOS*, 8: e6758) which can be used to select a BRAF inhibitor according to the invention.

The expression "an enhancer of HuR/ELAV protein" defines an agent capable of enhancing the levels of HuR/ELAV protein, in particular the cytoplasmic levels of HuR/ELAV protein, in particular an agent that induces an increase in cellular expression of HuR. Examples of agents enhancing the cytoplasmic expression of HuR include selective estrogen-receptor modulators (SERM) or PPAR agonists like those described in Roche et al., 2014, *Cellular Signalling*, 26, 433-443, in particular, PPARβ or δ (peroxisome-proliferator-activated receptor β or δ) agonist such as GW501516 (endurobol);

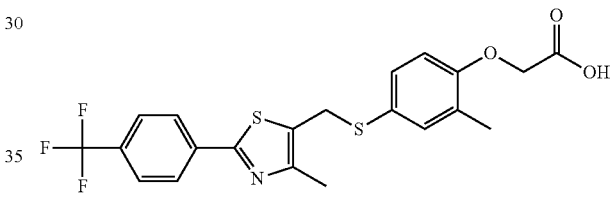

2-[2-methyl-4-[[4-methyl-2-[4-(trifluoromethyl)phenyl]-1,3-thiazol-5-yl]methylsulfanyl]phenoxy]acetic acid; lithium (Li) and salts thereof such as lithium carbonate

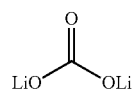

($Li_2CO_3$), lithium citrate

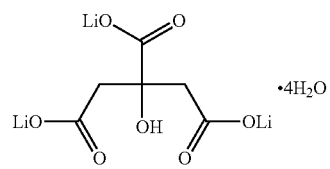

($Li_3C_6H_5O_7$), lithium sulfate

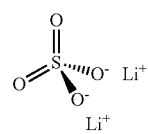

($Li_2SO_4$), lithium oxybutyrate

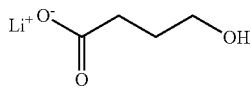

($C_4H_9LiO_3$), lithium orotate

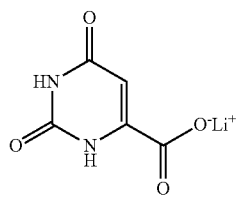

($C_5H_3LiN_2O_4$), and lithium hydroxybutyrate

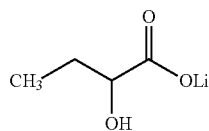

($C_4H_7LiO_3$). The ability of a compound to increase cellular expression of HuR, in particular in the cytoplasm can be assessed as described below, for example by western blot analysis performed on separated nuclear and cytoplasmic cell fractions or by a method of the invention.

Lithium (Li) is a chemical element and a soft, silvery-white alkali metal and lithium salts are commonly known as a medication for use in psychiatric disorders. Lithium has been shown to enhance the levels of HuR/ELAV protein in various cell types, HuR represses Wnt/β-catenin-mediated transcriptional activity by promoting cytoplasmic localization of β-catenin (Kim et al., 2015, *Biochem Biophys Res Commun.*, 457(1):65-70).

The expression "BRAF mutated solid tumor cancer" comprises cancers that present tumors presenting at least one BRAF point mutation. Examples of BRAF mutated solid tumor cancers comprise BRAF mutated melanomas (e.g. BRAF V600E mutation melanoma), BRAF mutated colorectal carcinoma (CRC), BRAF mutated papillary thyroid cancer (PTC) (e.g. BRAF V600E mutation PTC), BRAF mutated lung cancers, BRAF mutated papillary craniopharyngioma, classical hairy-cell leukaemia (HCL-C), metanephric kidney adenoma, ovarian cancer, glioma, ependymoma, non-Hodgkin lymphoma, liver, stomach or esophageal cancers.

A BRAF mutated cancer can be identified for example by using either PCR-based assays (allow the identification of most frequent mutations like V600E and V600K but miss the identification of patients with more rare mutations) or sequencing assays (Sanger or ideally NGS that will not miss BRAF mutations located outside codon V600). Alternatively, immunohistochemistry (IHC) staining using anti-BRAF V600E primary antibody is routinely used to detect BRAF V600E mutated tumors with sensitivity and specificity quiet comparable to sequencing and real-time PCR methods.

The term "melanoma" defines a type of cancer that develops from the pigment-containing cells known as melanocytes. Melanoma typically occurs in the skin but may occur in the mouth, intestines, or eye. Melanoma and in particular metastatic melanoma (stage IV melanoma) can be associated with BRAFV600 mutation, in particular BRAFV600E mutation (but not exclusively, other point mutations like BRAF-V600K and more rarely V600R and V600D mutations are more rarely detected).

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a melanoma in a mammal, particularly a human, and includes inhibiting the disease, i.e., arresting its development; or relieving the disease, i.e., causing regression of the disease and/or its symptoms or conditions such as improvement or remediation of damage.

The term "efficacy" of a treatment or method according to the invention can be measured based on changes in the course of disease or condition in response to a use or a method according to the invention. According to a particular embodiment, the efficacy of a combined use according to the invention can be measured through the assessment of efficacy of a BRAF inhibitor, in particular long term efficacy regarding repression of tumor growth, progression and dissemination, decrease of the number of cancer cells or their proliferation rate as compared to the efficacy of the same BRAF inhibitor alone. According to another embodiment, the efficacy of a combined use according to the invention can be assessed by the observation of a decrease or inhibition of the emergence of an adaptive resistance of cancer cells under treatment with a BRAF inhibitor, for example by clinical observation of maintained response to BRAF inhibitors and resistant disease becoming responsive to BRAF inhibitors after treatment discontinuation also any in vivo assessment, using immunohistochemistry, to detect preventive effect on the BRAF inhibitors-induced expression of indicators of reversible acquired resistance. This includes in vivo expression analysis of markers that relate to retained dependency on ERK signaling: overexpression of surface RTK receptors i.e.: EGFR, PDGFRB, IGF1R, elevated CRAF activity and expression, increased pERK1/2, increased pMEK, increased levels of COT/Tpl2 and those that indicate activation of alternative pathways: i.e.: pAKT, and other markers involved in the PI3K pathway, including common downstream markers of adaptive response like components of the eIF4F eukaryotic translation complex and its regulators like 4EBP1/p4EBP1.

According to another aspect, the efficacy of a combined use according to the invention can be assessed through the observation of a decrease in cancer heterogeneity, for example in recently developed animal models such as described in Blackburn and Langenau, 2014, *Dis Model Mech*, 7: 755-62 as compared to use of a BRAF inhibitor alone. Beside animal models, in vivo assessment of tumor heterogeneity can be also conducted using single-cell transcriptomic methodologies like for example stochastic profiling, based on small-population averaging of randomly chosen cells that can be isolated using laser-captured microdissection as described in Wang et al, 2013 *Nature Protoc*, 8: 282-301 or immunohistochemistry and high-throughput proteomic methods that allow the simultaneous expression analysis of the above listed markers of adaptive response at single-cell level like for example high-resolution laser ablation coupled to mass cytometry (also called spatial or imaging mass cytometry) as described in Giesen et al, 2014, *Nature Methods* 11:417-22.

The term "subject" as used herein refers to mammals. For examples, mammals contemplated by the present invention include human, primates, domesticated animals such as cattle, sheep, pigs, horses, laboratory rodents, other pets and the like.

Combined Use and Combined Compositions

The invention provides pharmaceutical or therapeutic agents as compositions and methods useful for the treatment of a BRAF-mutated cancer.

In a particular embodiment, the invention provides a use of at least one enhancer of HuR/ELAV protein for the treatment of a BRAF-mutated cancer, wherein said enhancer is to be administered in combination with at least one BRAF inhibitor.

In a further particular embodiment, the said at least one enhancer of HuR/ELAV protein is selected from a selective estrogen-receptor modulator, a PPARβ or δ agonist such as GW501516 and lithium (Li) and salts thereof or a mixture of at least two of those.

In another further particular embodiment, the said at least one enhancer of HuR/ELAV protein is selected from a selective estrogen-receptor modulator and a PPARβ or δ agonist such as GW501516 or a mixture of at least two of those.

In another further particular embodiment, the said at least one enhancer of HuR/ELAV protein is lithium (Li) or a salt thereof, such as Li Carbonate.

In another further particular embodiment, the said at least one BRAF inhibitor is selected from vemurafenib or a precursor thereof, encorafenib, GDC0879, CEP-32496 and dabrafenib or a mixture of at least two of those.

In a further particular embodiment, the BRAF inhibitor is vemurafenib.

The invention encompasses the use of at least one enhancer of HuR/ELAV protein or a pharmaceutical formulation thereof, wherein said at least one enhancer is to be administered to an individual simultaneously or sequentially with at least one BRAF inhibitor (e.g. multiple drug regimens). Said at least one enhancer of HuR/ELAV protein or a pharmaceutical formulation thereof that is administered simultaneously with said at least one BRAF inhibitor can be administered in the same or different composition(s) and by the same or different route(s) of administration.

Compositions of this invention may further comprise one or more pharmaceutically acceptable additional ingredient(s) such as alum, stabilizers, antimicrobial agents, buffers, coloring agents, flavoring agents, adjuvants, and the like.

The compositions according to the invention, together with a conventionally employed adjuvant, carrier, diluent or excipient may be placed into the form of pharmaceutical compositions and may be employed as solids, such as tablets or filled capsules, or liquids such as solutions, suspensions, ointments, emulsions, elixirs, or capsules filled with the same, films or gels, all for oral use. The compositions may also be formulated as a dry product for reconstitution with water or other suitable vehicle before use.

Compositions of this invention as liquid formulations including, but not limited to, aqueous or oily suspensions, solutions, emulsions, syrups, and elixirs.

Such liquid preparations may contain additives including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Preservatives include, but are not limited to, methyl or propyl p-hydroxybenzoate and sorbic acid. Dispersing or wetting agents include but are not limited to poly(ethylene glycol), glycerol, bovine serum albumin, Tween®, Span®.

Further materials as well as formulation processing techniques and the like are set out in *The Science and Practice of Pharmacy* (Remington: *The Science & Practice of Pharmacy*), $22^{nd}$ Edition, 2012, Lloyd, Ed. Allen, Pharmaceutical Press, which is incorporated herein by reference.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, acacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycolate. Wetting agents include, but are not limited to, sodium lauryl sulfate. Tablets may be coated according to methods well known in the art.

In a particular embodiment, the invention provides a pharmaceutical formulation according to the invention for use as a medicament.

Mode of Administration

Enhancers of HuR/ELAV protein and BRAF inhibitors of this invention may be administered independently any manner by oral route including to the mucosal surfaces of the oral cavity including the gingiva, the floor of the oral cavity, cheeks, lips, tongue, teeth.

Enhancers of HuR/ELAV protein and BRAF inhibitors of this invention may be administered independently in any manner by intravenous or intra-muscular or sub-cutaneous injection.

Patients

In an embodiment, patients according to the invention are patients suffering from a BRAF mutated solid tumor cancer.

In an embodiment, patients according to the invention are patients suffering from a BRAF BRAF V600 mutated cancer, in particular a BRAF V600E mutated cancer.

In another further embodiment, patients according to the invention are patients suffering from a BRAF mutated melanoma.

In another further embodiment, patients according to the invention are patients suffering from a BRAF mutated papillary thyroid cancer (PTC).

In another further embodiment, patients according to the invention are patients suffering from a BRAF mutated colorectal carcinoma (CRC).

In another further embodiment, patients according to the invention are patients suffering from a cancer selected from BRAF mutated papillary craniopharyngioma, classical hairy-cell leukaemia (HCL-C), metanephric kidney adenoma, lung cancers, ovarian cancer, glioma, ependymoma, non-Hodgkin lymphoma, liver, stomach and esophageal cancers.

Use According to the Invention

In a particular embodiment, the combined use of at least one enhancer of HuR/ELAV protein and at least one BRAF inhibitor according to the invention decreases the cancer cell heterogeneity.

In another particular embodiment, the combined use of at least one enhancer of HuR/ELAV protein and at least one BRAF inhibitor according to the invention prevents the emerging of adaptive BRAF therapy resistance.

In another particular embodiment, the combined use of at least one enhancer of HuR/ELAV protein and at least one BRAF inhibitor according to the invention leads to a synchronization of tumor cells in cell cycle phase where the toxicity of said BRAF inhibitor is increased and thereby increases the toxicity of said BRAF inhibitor to cancer cells.

In another embodiment, the invention provides a method of treatment of a BRAF mutated solid tumor cancer in a subject, said method comprising the administration of a therapeutically effective amount of at least one enhancer of HuR/ELAV protein or any suitable pharmaceutically acceptable formulation thereof, in a subject, in particular a mammal in need thereof, wherein said at least one enhancer of HuR/ELAV protein or any suitable pharmaceutically acceptable formulation thereof is to be administered in combination with at least one BRAF inhibitor.

In another embodiment, the invention provides a method of prevention of the emerging of adaptive BRAF therapy resistance, said method comprising the administration of a therapeutically effective amount of at least one enhancer of HuR/ELAV protein or any suitable pharmaceutically acceptable formulation thereof, in a subject, in particular a mammal, suffering from a BRAF mutated solid tumor cancer, wherein said at least one enhancer of HuR/ELAV protein or any suitable pharmaceutically acceptable formulation thereof is to be administered in combination with at least one BRAF inhibitor.

In another embodiment, is provided a compound, a use or a method according to the invention, wherein the disorder is a BRAF mutated melanoma.

In an embodiment, the invention provides a method of identifying agents useful in the potentiation of therapeutic effects of BRAF inhibitors, said method comprising the steps of:
a) providing isolated mutated cancer cells (such as V600E mutated cells);
b) contacting said candidate agent with said mutated cancer cells in combination with a BRAF inhibitor; and
c) determining the ability of the said agent to increase HuR cell expression and/or cytoplasmic content of the cancer cells without affecting substantially their proliferation rate compared to HuR cell expression and/or cytoplasmic content in absence of said agent; wherein the ability of an agent to increase HuR cell expression and/or cytoplasmic content of the cancer cells is indicative of an agent that is capable of suppressing paradoxical proliferation in cancer cells in combination with a BRAF inhibitor, and/or
c') when said cells are capable of generating a paradoxical proliferation response in presence of a BRAF inhibitor and in absence of agent, determining the ability of said agent, when contacted under step b) at a concentration where HuR cell expression and/or cytoplasmic content of the cancer cells is increased without affecting substantially their proliferation rate, to suppress paradoxical proliferation in said cells compared to control in combination with a BRAF inhibitor alone; wherein the ability of an agent to suppress paradoxical proliferation is indicative of an agent that is capable of preventing the arising of resistance to BRAF inhibitor administration.

In another embodiment, the invention provides a method of identifying agents useful in the potentiation of therapeutic effects of BRAF inhibitors, said method comprising the steps of:
a) providing isolated mutated cancer cells (such as V600E mutated cells);
b) contacting said candidate agent with said mutated cancer cells in combination with a BRAF inhibitor; and
c) determining the ability of the said agent to increase HuR cell expression and/or cytoplasmic content of the cancer cells without affecting substantially their proliferation rate compared to HuR cell expression and/or cytoplasmic content in absence of said agent; wherein the ability of an agent to increase HuR cell expression and/or cytoplasmic content of the cancer cells is indicative of an agent that is capable of suppressing paradoxical proliferation in cancer cells in combination with a BRAF inhibitor.

In another embodiment, the invention provides a method of identifying agents useful in the potentiation of therapeutic effects of BRAF inhibitors, said method comprising the steps of:
a') providing isolated mutated cancer cells (such as V600E mutated cells) capable of generating a paradoxical proliferation response in presence of a BRAF inhibitor and in absence of agent (e.g. such as A375 cells used herein);
b') contacting said candidate agent at a concentration at which the said agent is able to increase HuR cell expression and/or cytoplasmic content of the cancer cells without affecting substantially their proliferation rate in combination with a BRAF inhibitor; and
c') determining the ability of said agent to suppress paradoxical proliferation in said cells compared to control in combination with a BRAF inhibitor alone; wherein the ability of an agent to suppress paradoxical proliferation is indicative of an agent that is capable of preventing the arising of resistance to BRAF inhibitor administration.

According to a particular embodiment, the increase cellular expression of HuR, in particular in the cytoplasm can be assessed by using 1) cell fractionation to separate nucleus from cytosol combined with western-blot analysis of HuR content in each of these fractions 2) Immunocytochemistry (ICC) to visualize the nuclear versus cytoplasmic content of HuR under the effect of a compound. The sensitivity of this assay can be improved by an adenovirus-mediated overexpression of an epitope-tagged HuR construct inserted in the adenovirus followed by monitoring in ICC the expression of the exogenous epitope-tagged HuR.

According to a particular embodiment, a method of identifying agents useful in the potentiation of therapeutic effects of BRAF inhibitors according to the invention is more sensitive when carrying out step c') by determining the ability of said agent, when combined with a BRAF inhibitor, to suppress paradoxical proliferation in said mutated cancer cells infected with an adenovirus overexpressing a control protein (e.g. GFP), those cells generating a paradoxical proliferation response in presence of a BRAF inhibitor and without said agent (positive control for paradoxical proliferation), while comparing with a positive control for paradoxical proliferation inhibition (negative control for paradoxical proliferation) being the same cells infected with an HuR overexpressing adenovirus contacted with a BRAF inhibitor alone. According to this particular aspect, the adenovirus overexpressing a control protein decreases the baseline proliferation signal, for example in melanoma cancer cells like in A375 cells but renders the detection of paradoxical proliferation and its suppression more easily detectable.

These assays can be conducted using an automated large screening platform for multiple agent-testing using a 96 well format. In such multiple agent-testing using a 96 well format, signals can be carried in an ELISA microplate reader.

According to a particular aspect, a method of identifying agents useful in the potentiation of therapeutic effects of BRAF inhibitors according to the invention might be used as high throughput assays.

For example, in a method according to the invention, candidate agents are first assayed for their capacity to increase HuR cell expression and/or cytoplasmic signal according to step c). In particular, the sensitivity of this step can be increased though the use of a HuR tagged construct used in the present examples where the Tag signal is detected. Second, a method according to the invention can be applied to compounds which are first selected based on their capacity to increase HuR cytoplasmic content. In this case, those first selected compounds are used as candidate agents in a method of the invention their ability to suppress paradoxical proliferation in cancer cells, when combined with a BRAF inhibitor, is compared to control in combination with a BRAF inhibitor alone is assayed according to step c').

According to a particular aspect, is provided a method of identifying agents useful in the potentiation of therapeutic effects of BRAF inhibitors according to the invention wherein steps c and c' are conducted.

In another embodiment, the effect of a candidate agent identified in a method according to the invention can be confirmed by the monitoring of mutated cell proliferation and relative (percentage) survival of the mutated cells in a cell proliferation assay (dose response analysis) in which the combined administration of a HuR enhancer according to the invention with a BRAF inhibitor will be compared to the effect of said BRAF inhibitor alone.

The suppression of paradoxical proliferation or reduced half-maximal growth-inhibitory concentration ($IG_{50}$) can be also assessed under HuR siRNA knockdown conditions to confirm the HuR mediated effect of the candidate agent.

According to a particular embodiment, mutated cancer cells used in a method of the invention can be BRAFV600E mutated melanoma cells like the A375 melanoma cell line in which a paradoxical proliferation occurs in regular proliferation assays or other melanoma cells or resistant BRAFV600E mutated non melanoma cell lines in which reduced $IG_{50}$ can be observed.

The methods of the invention of identifying agents useful in the potentiation of therapeutic effects of BRAF inhibitors according to the invention are particularly useful since they allow large screening campaign of agents in a high throughput manner.

Examples illustrating the invention will be described hereinafter in a more detailed manner and by reference to the embodiments represented in the Figures.

EXAMPLES

The following abbreviations refer respectively to the definitions below:

A375 cells (BRAFV600E melanoma cell line), aG (vector expressing GFP), aG cells (aG-infected A375 cells), aGnt (excipient-treated aG cells), aGt (vemurafenib-treated aG cells), aH (vector overexpressing a T7 epitope-tagged HuR), aH cells (aH-infected A375 cells), aHnt (excipient-treated aH cells), aHt (vemurafenib-treated aH cells), BRAF (serine/threonine-protein kinase B-Raf), BRAFV600E (BRAF V600E mutation), BSA (bovine serum albumin), c-Myc (a regulator gene that codes for a transcription factor), cisPt194 (Cisplatin 194), DAPI (4',6-diamidino-2-phenylindole), DFMO (eflornithine), DMSO (dimethyl sulfoxide), EGFR (growth factor receptor), eIF4E (eukaryotic translation initiation factor 4E), FACS (fluorescence-activated cell sorting), FBS (fetal bovine serum), GFP (green fluorescent protein), HuR (Human antigen R, RNA-binding protein), HuR-siRNA (small interfering RNA targeting HuR) Ki67 (Ki67 protein, proliferation marker), Li (lithium), m.o.i. (multiplicity of infection), NDS (normal donkey serum), NI (non-infected), p21 (cyclin-dependent kinase inhibitor 1 or CDK-interacting protein 1), p53 (tumor protein p53), p4EBP1 (phospho-eIF4E-binding protein 1), pAKT (protein kinase B), PI (propodium-iodide), PBS (phosphate-buffered saline), PDGFRB (Platelet-derived growth factor receptor β), pERK1/2 (phospho-Extracellular Signal-Regulated Kinase1/2), siRNA (small interfering RNA), Sp1 (fast-proliferating subpopulation), Sp2 (intermediary mild-proliferating subpopulation), Sp3 (slow-proliferating subpopulation), Sp4 (quiescent/slow-proliferating subpopulation), SPADE (a spanning-tree progression analysis of density-normalized events), viSNE (visual interactive Stochastic Neighbor Embedding).

Example 1: HuR Overexpression in A375 Melanoma Cells Treated with Low-Dose BRAF Inhibitor The effect of HuR overexpression on the emergence of paradoxically proliferative subpopulations in A375 melanoma cells treated at a low-dose of vemurafenib was tested.

Cell Lines and Culture.

The A375 BRAFV600E melanoma cell line was purchased from CLS Cell Lines Service GmbH (Cryovial: 300110). A375 cells were maintained at 37° C. and 5% $CO_2$ in a humidified atmosphere and grown in DMEM (Dulbecco's modified Eagle's medium) growth media supplemented with 10% FBS (fetal bovine serum), 2 mM glutamine, 1% penicillin/streptomycin. Cells were verified to be mycoplasma-free (PanReac Applichem mycoplasma test kit). Cells were treated with the BRAF inhibitor, vemurafenib (Selleckchem), also known as N-[3-[5-(4-chlorophenyl)-1H-pyrrolo[2,3-b]pyridine-3-carbonyl]-2,4-difluorophenyl] propane-1-sulfonamide and dissolved in dimethyl sulphoxide (DMSO, 10 mM storing concentration).

Cell Proliferation Assay.

Cell proliferation was measured using WST-1 reagent (Roche applied Science). Melanoma cells were plated (2500 cells per well) in 96-well tissue culture plates. After 24 h, the cells were treated with vemurafenib or DMSO (excipient) at the indicated concentrations in triplicate or quadruplicate. The excipient is used at the same dilution as the one necessary to get the desired concentration of vemurafenib, in that case for example if 1/1000 dilution is necessary to get a 100 nM final concentration of vemurafenib, then the DMSO pure stock solution will be also diluted to 1/1000. For the standard proliferation assays, after the treatment period of 48 h, WST-reagent (20 μl, 10% of the final volume) was added to the wells and incubated at 37° C. for 1 to 2 h depending on the experiment in order to stay within the linear range of the assay. The plates were read at 450(−650)

nm on a $V_{max}$ kinetic ELISA Microplate Reader (Molecular Devices). Cell proliferation is expressed as percentage of the absorbance compared with the DMSO-treated cells. Proliferation assays for overexpression experiments were scheduled as follows: A375 cells were plated (800000 cells per well) in six-well culture plates. After 24 h, the cells were infected overnight at indicated m.o.i. (multiplicity of infection) (in 3 ml medium), transferred the next morning in 96-well culture plates (2500 cells per well) and left for 24 h before being treated as indicated above. For western blot analysis, cells were left in the six-well culture plates for an additional 24 h before being harvested (48 h post-infection). For cell cycle, cell death determination and mass cytometry experiments, the content of each well from the six-well plates used for overnight infection was transferred to a 10 cm culture dish and left for 24 h before being treated for either 24 h (cell cycle, cell death determination and mass cytometry experiments) or 48 h (cell death determination) at the indicated concentrations and then harvested.

Western Blot Analysis.

Western blot analysis was performed on cell extracts of A375 cells at 48 h post-infection. Whole cell lysates were prepared using RIPA (radioimmunoprecipitation assay) buffer (PBS (phosphate-buffered saline), 1% NP40 (nonyl phenoxypolyethoxylethanol 40), 0.1% sodium deoxycholate, 0.1% SDS (sodium dodecyl sulphate)) supplemented with fresh protease and phosphatase inhibitors (easy packs tablets, Roche). Cell lysates were quantified for protein content using Bio-Rad DC (detergent compatible) kit. Protein samples were resolved on 12.5% polyacrylamide Bis-Tris gel (Bio-rad) and then transferred to nitrocellulose membrane. After saturation, the membranes were incubated overnight with the anti-HuR mouse monoclonal antibody (Santa-Cruz/3A2-sc-5261, 1:1000) raised against full-length HuR of human origin. The secondary antibody conjugated to horseradish-peroxidase (Bio-Rad goat anti-mouse IgG-HRP, 1:3000) was incubated at room temperature for 30 minutes. Blots were developed using the ECL (enhanced chemiluminescent) system (Thermo-Scientific) according to the manufacturer's instructions. Anti-α-tubulin mouse monoclonal antibody was used as a control (Clone B-5-1-2, 1:10000/Sigma Aldrich).

Adenovirus Construct and Virus Stock Preparation.

Adenoviruses expressing GFP (green fluorescent protein) or T7 epitope-tagged (gene 10 leader peptide) HuR were generated as previously described (Sutterlüty et al., 1999, *Nat Cell Biol*, 1:207-14; Hardy et al., 1997, *J Virol*, 71: 1842-49). An originally subcloned T7 epitope-HuR fragment, was isolated by an Nhe1/Xba1 digestion and subcloned into the Xba1 site of pAdlox vector. Successful cloning was verified by sequencing. Recombinant viruses were generated by co-transfecting pAdlox-T7 epitope HuR plasmid DNA, digested previously with SfiI, and Ψ5 adenovirus DNA into 293-CRE8 cells (Cre-expressing Human embryonic kidney 293 cells) as described (Sutterlüty et al., 1999, supra). Recombinant adenoviruses were selected by serial re-infection in 293-CRE8 cells and finally amplified in 293 cells and purified by CsCl density-gradient centrifugation. Infectious virus particles were calculated by determining the optical density and A375 cells were infected with an m.o.i. (multiplicity of infection) of 5 and 25 (an m.o.i. of 125 was also tested in western blot analysis). AdGFP virus (adenovirus encoding GFP) was generated using the same procedure after subcloning the eGFP (enhanced GFP) from pEGFPC1 (red-shifted variant of wild-type GFP) via NdeI/EcoR1 into pAdlox.

Cell Death Quantification and Cell Cycle Analysis.

Cells were harvested using Versene (EDTA solution 0.48 mM in Phosphate Buffered solution, Gibco, ThermoFisher Scientific), transferred to FACS (fluorescence-activated cell sorting) tubes, stained using the propodium Iodide (PI)/Annexin V Apoptosis Detection Kit APC (Affymetrix eBioscience) according to the manufacturer's instructions. 25000 events were analyzed for each sample by flow cytometry using the BD Accura C6 equipment and software. For cell cycle analysis, the PI/RNase Staining Buffer (BD Pharmigen) was used according to the manufacturer's instructions. Cell cycle FCS files were additionally analyzed using the Dean-Jett-Fox model in the FlowJo software (FLOWJO, LLC).

Immunofluorescence Staining.

A375 cells were plated (800000 cells per well) on coverslips in six-well culture plates. After 24 h, the cells were infected as indicated above. After 48 h, coverslips were transferred to 12-well plates. Cells were washed in PBS and fixed in PBS containing 4% paraformaldehyde for 30 minutes at room temperature. After further washing with PBS (containing 0.1% BSA (bovine serum albumin)), cells were permeabilized with blocking PBS containing 0.3% Triton X-100 and 10% Normal Donkey Serum (NDS) for 45 minutes. Cells were incubated with polyclonal goat anti-T7 epitope antibody (LSBio, 1:200) in blocking buffer (PBS, 1% BSA, 1% NDS, 0.3% Triton X-100) for 1 h at room temperature, followed by incubation with donkey anti-goat Alexa Fluor 568 (Invitrogen, ThermoFisher Scientific, 1:500) for 1 h. The cells were washed in PBS, stained with DAPI-(4',6-diamidino-2-phenylindole)-Fluoromount-G (Southern Biotech), mounted on glass slides and observed under confocal LSM700 microscope (Zeiss). GFP, Alexa 568 and DAPI signals and images were analyzed with the ZEN software (Zeiss).

Mass Cytometry Analysis.

Pre-validated and pre-titrated metal-conjugated antibodies were purchased from Fluidigm. The metal tag selection was optimized using the Maxpar panel designer (Fluidigm). Cells (grown in 10 cm dishes, as described in cell proliferation assay section) were washed three times with PBS, incubated with Versene for 5 min at 37° C., washed again and transferred to FACS tubes. After centrifugation, cells were resuspended in PBS and counted. In order to eliminate debris and most part of dead cells, samples were submitted to a standard Ficoll extraction protocol, before being resuspended in PBS and counted again. Stainings were conducted according to Maxpar staining protocols. $3.10^6$ cells of each sample were resuspended in serum-free medium containing Cisplatin-$^{194}$Pt (Fluidigm) at final concentration of 5 μM and incubated for 5 min at 37° C. Cisplatin staining was quenched by washing the cells with pre-warmed PBS supplemented with 10% FBS. After a second wash with PBS, cells were fixed in 500 μl of Maxpar Fix 1 buffer for 10 min at room temperature, centrifuged and resuspended in 50 μl of Maxpar cell staining buffer (CSB). Samples were mixed with an equal volume of master mix of metal-conjugated antibodies directed against cell surface markers i.e. $^{170}$Er-anti-EGFR (clone AY13)/$^{156}$Gd-anti-CD140b (PDGFRB (Platelet-derived growth factor receptor (β)) (clone18A2) and left for 30 min at room temperature. Master mix was prepared as recommended by the manufacturer (final dilution of antibodies 1:100, 1 μl of pre-titrated antibody diluted in 50 μl of CSB for each sample). After one additional washing with CSB, samples were placed on ice for 10 min to chill. Cells were then further permeabilized by adding 1 ml of pre-chilled 70% methanol. Following 15 min incubation on ice, cells were washed twice with CSB, resuspended in 50 µl of CSB and mixed with an equal volume of master mix prepared as above containing the $^{168}$Er-anti-Ki67 antibodies. Following 30 min incubation at room temperature, 500 µl of DNA intercalator solution (125 nM final concentration, Cell-ID Intercalator-$^{191/193}$Ir, Fluidigm) was added to each sample. After additional 15 min incubation at room temperature, cells were washed with CSB and twice with deionized water. Pellets were stored at 4° C. Prior to mass cytometry analysis, cells were adjusted to 2.5-5.10$^5$/ml in deionized water, mixed with EQ four element calibration beads (Fluidigm) containing $^{140/142}$Ce, $^{151/153}$Eu, $^{165}$Ho and $^{175/176}$Lu and filtered with cell strainer caps. Samples were run on CyTOF 2 mass cytometer (Fluidigm). Normalized data were first analyzed with software available through Cytobank (see Worldwide Website: cytobank.org). Live singlets were gated on Cis-$^{194}$Pt staining (dead cells exclusion) (Fienberg et al., 2012, *Cytometry*, 81:467-75) and $^{191/193}$Ir staining (DNA content, debris and doublets exclusion). viSNE (visual interactive Stochastic Neighbor Embedding maps) and SPADE (a spanning-tree progression analysis of density-normalized events) spanning-trees were generated. The tSNE (t-distributed stochastic neighbor embedding) default parameters were: iterations 1000, perplexity: 30, theta: 0.5. Data in FCS format were exported to the software environment R for graphic production and statistical computing.

Figure 1:
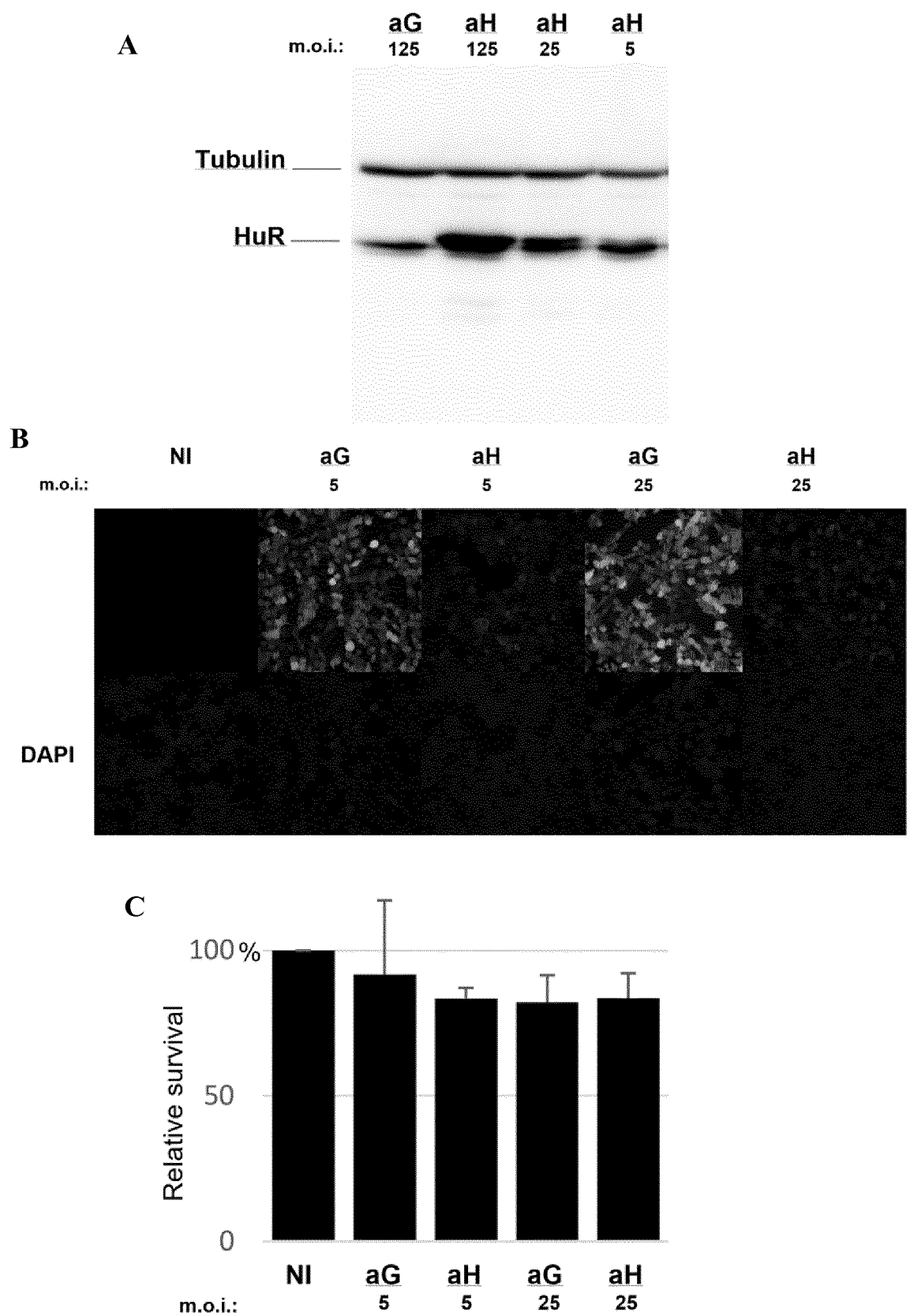
FIG. 1 shows optimal adenovirus m.o.i determination for the overexpression of HuR without affecting A375 cell proliferation rate as described in Example 1. A: western-blot analysis on cells infected with aG or aH at m.o.i 5, 25 or 125; B: GFP fluorescence in a control adenovirus (aG)-infected cells and T7 epitope tag staining in aH-infected cells at m.o.i. 5 or 25 compared to non-infected (NI) cells; C: relative survival of the aG or aH-infected A375 cells (at m.o.i. 5 or 25) compared with NI cells, as measured using WST-1 reagent cell proliferation assay.

A Cre-lox recombined (Hardy et al., 1997, supra) adenovirus construct for the efficient overexpression of a T7 epitope-tagged HuR (aH) was prepared. A similar vector expressing GFP was also prepared as a control (aG) (FIGS. 1 A, B). A series of assays was conducted to verify that the m.o.i. used in experiments did not significantly affect the proliferation rate of the aH- or aG-infected A375 cells (aH and aG cells) compared with the non-infected (NI) cells (FIG. 1C) in order to determine the optimal adenovirus multiplicity of infection (m.o.i.) for the overexpression of HuR without affecting the A375 proliferation rate. The aH and aG virus preparations were similarly titrated (90% and 100% positive staining respectively at m.o.i. 5 and 25 for both constructs) and cells were homogenously stained (i.e. infected) with either construct, including at the lowest adenovirus concentration (m.o.i. 5) used in experiments (FIG. 1B).

Figure 2:
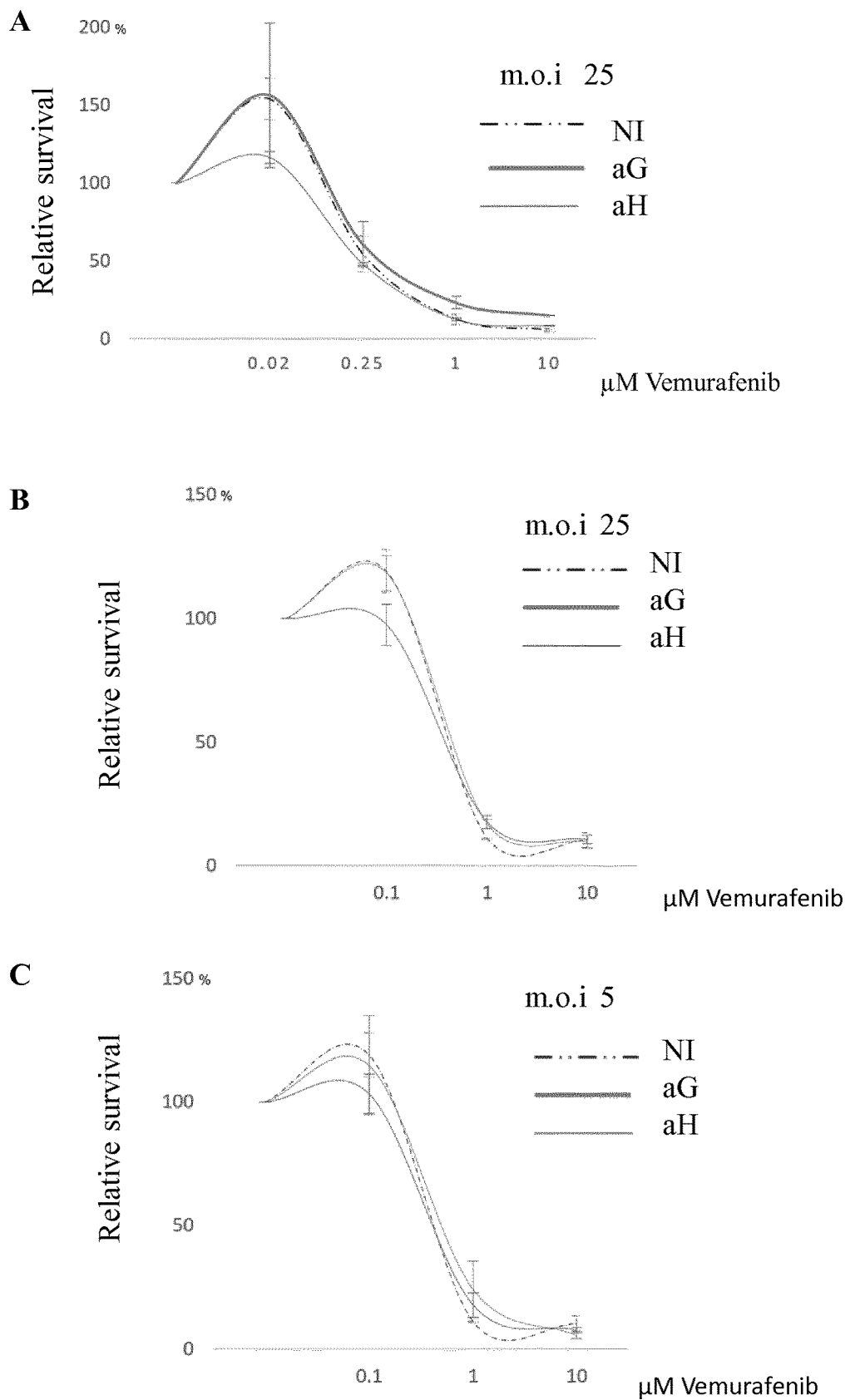
FIG. 2 shows vemurafenib dose response assessed by the relative survival of A375 cells as measured by WST-1 reagent cell proliferation assay of NI cells, control adenovirus (aG) or (aH) infected cells at m.o.i 25 (A & B) or 5 (C) as described in Example 1.

It was reproducibly observed that some BRAF-mutated sensitive melanoma cell lines treated with low-dose (sub-optimal) vemurafenib (i.e. 20 nM and up to 100 nM depending on the cell lines) may paradoxically proliferate. This observation was repeatedly made in the A375 sensitive melanoma cell line (FIG. 2). Depending on the experiment, the proliferation rate increased to up to 50% at doses of 20 nM vemurafenib, and to a lower extent at 100 nM (up to about 25% at which the expected inhibition also occurred. As shown in FIG. 2, strikingly, no vemurafenib-induced paradoxical proliferation was observed in the aH cells in contrast to the aG or non-infected cells. This suppression of paradoxical proliferation varied with the level of HuR overexpression. Comparison of FIG. 2A to 2B indicates an inverse dose-effect of vemurafenib on paradoxical proliferation, indicating that the likelihood of occurrence of paradoxical proliferation is higher at lower dose than at higher concentration in a sensitive cell line; Comparison of FIG. 2B to 2C indicates a dose-suppressive effect of HuR overexpression on paradoxical proliferation.

Figure 3:
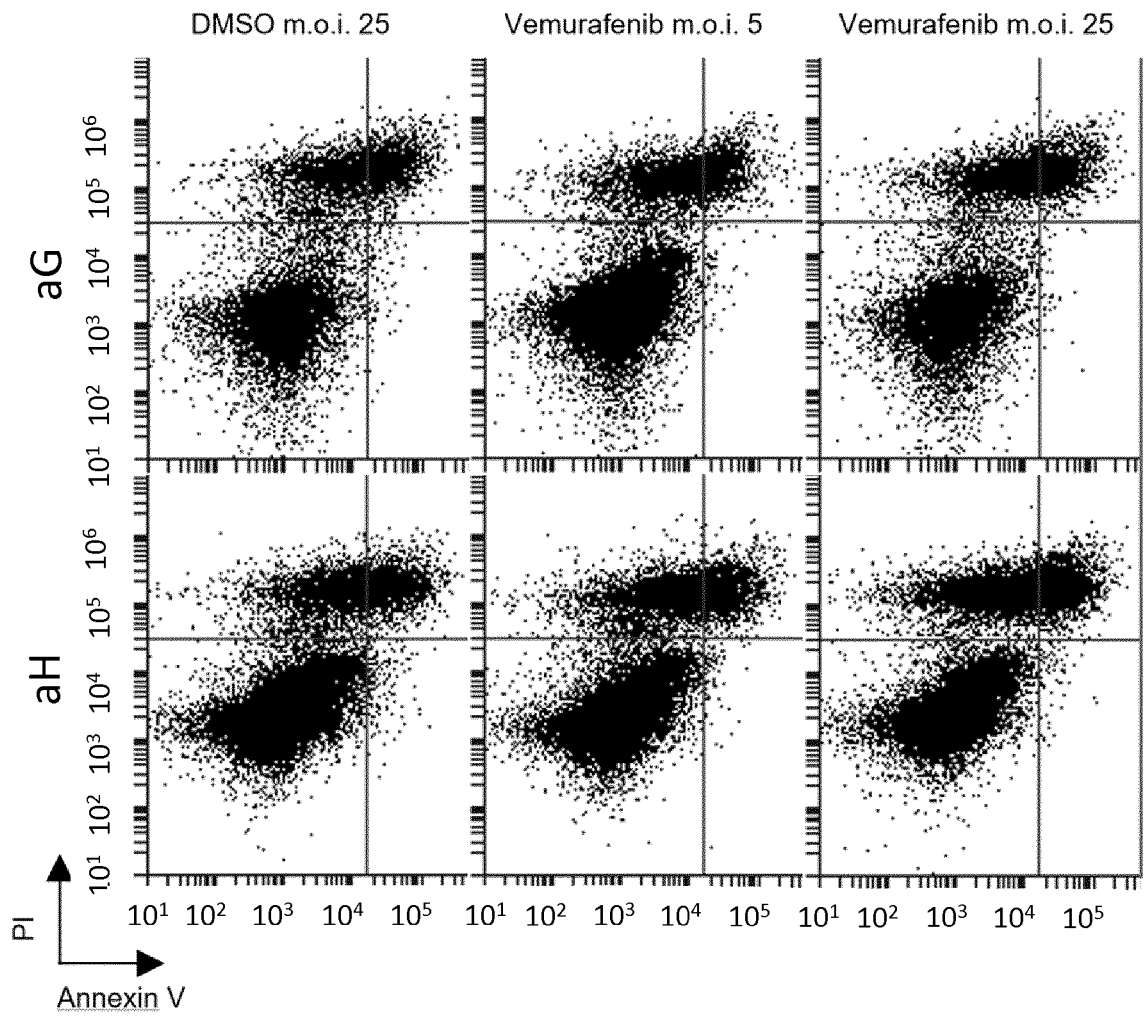
FIG. 3 shows the cell death rate (A) or cell cycle profile (B) in A375 melanoma cells in cells overexpressing HuR (aH infected cells) as compared to control (aG infected cells) when treated at low-dose vemurafenib or with DMSO, measured by flow cytometry analysis (A) or mass cytometry (B) as described in Example 1. A1: Flow cytometry analysis of double-stained propodium-iodide (PI) and Annexin V of cells infected at m.o.i. 5 or 25 treated with vemurafenib at 100 nM or with DMSO at the same final dilution as the one obtained in the drug treated sample. A2: Cell death quantification (%) as obtained from the flow cytometry results (25'000 events analyzed for each sample): black portion of the histograms: percentage of Annexin V positive cells within the percentage of dead cells (gray plus black). Respective percentages are indicated in the black portion of the histograms. B: Cell cycle analysis gated on live cells with PI staining, as described in Example 1 on aG and aH cells infected at m.o.i. 25 and treated with vemurafenib at the 20 nM or 100 nM or DMSO and stained with PI. Corresponding percentage of cells in each phase is indicated with histograms.
Figure 3:
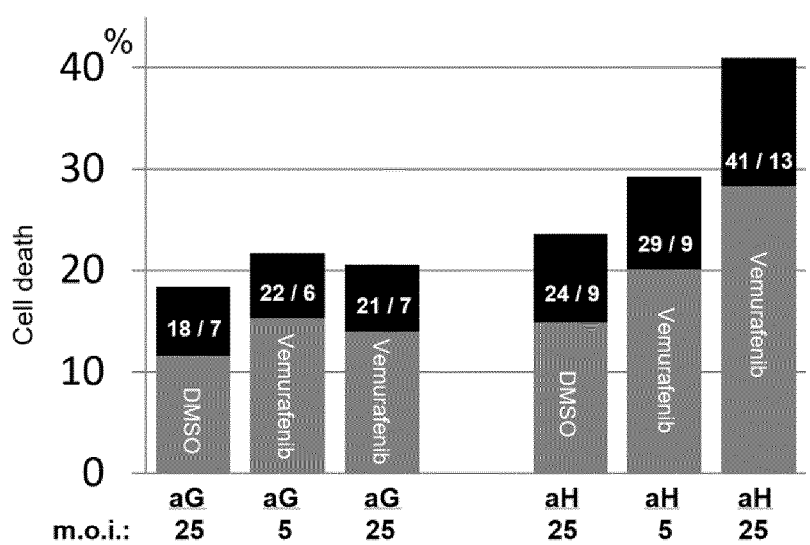
Figure 3:
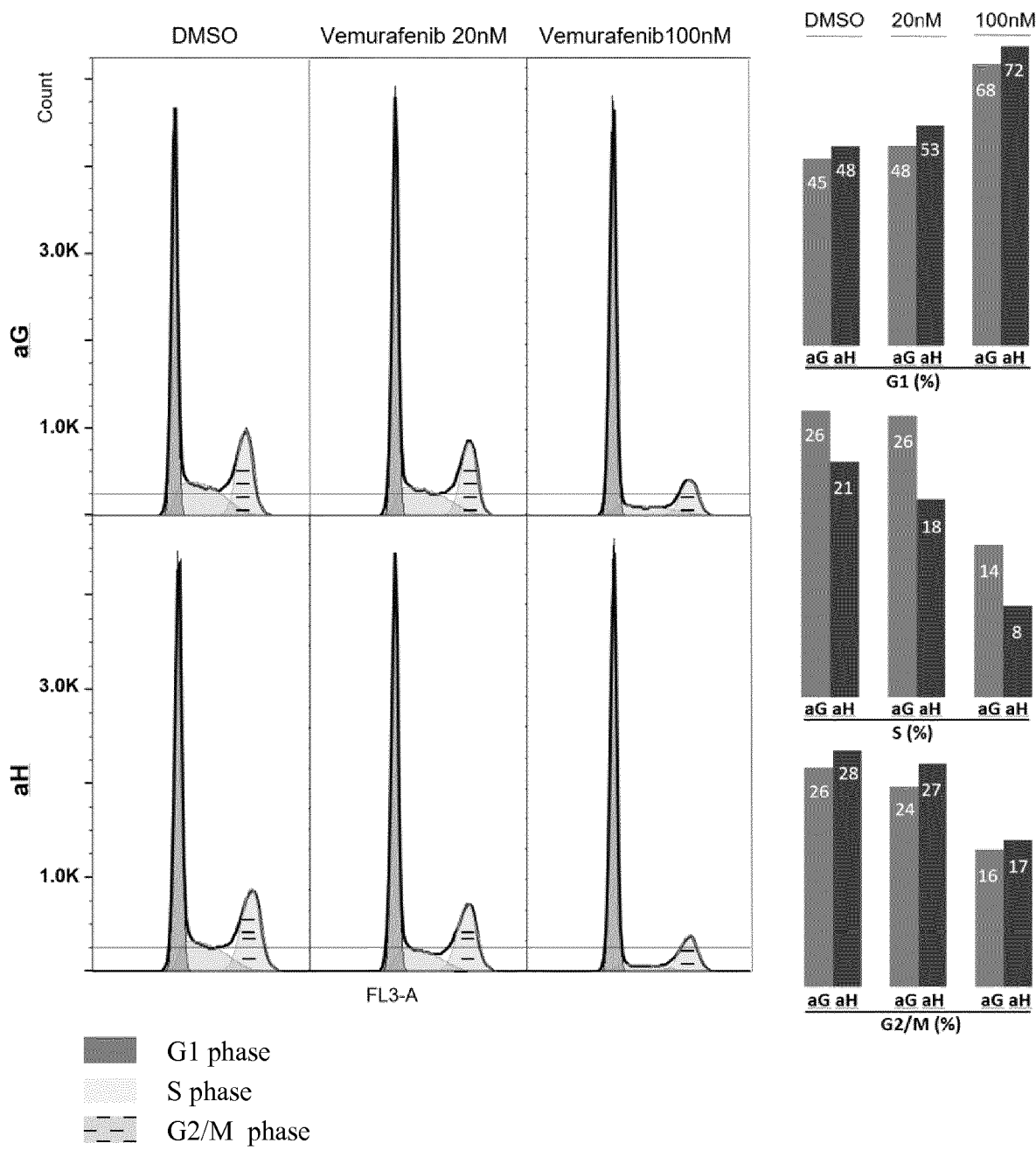

To confirm this effect, it was tested for an equivalent difference in terms of the death rate or the cell cycle profile of aH and aG cells. As shown in FIGS. 3A1 & A2, the death rate was higher in aH cells than in aG cells at 48 h post-treatment with a dose-dependent effect similar to that observed in the proliferation assays, varying with the level of HuR overexpression. Annexin V staining indicated that some dead cells were late apoptotic cells. However, the percentage of Annexin V-positive cells among the dead cells was not affected by HuR overexpression. Cell cycle analysis using propidium iodide (PI) flow cytometric staining was performed at m.o.i. 25, the value at which the maximum difference in death rate occurred (FIG. 3B). The main difference was a lower percentage of cells in the S phase (synthesis phase) in aH than in aG-treated cells across DMSO, vemurafenib 20 nM or vemurafenib 100 nM treated groups. This difference depended on the vemurafenib concentration, the difference being even more detectable at higher vemurafenib concentration. There was no corresponding cell percentage increase in the G1 phase (the first phase of cell cycle when the cell is still responsive to its environment) or decrease in the G2/M phase (follows S phase). Therefore, in aH-treated cells, G2/M accumulation is likely more important and death rate most likely higher for the cells being in S phase. It is important to notice that these moderate percentage differences in death rate and cell cycle profile are consistent with the expected ones from the proliferation assays.

Figure 4:
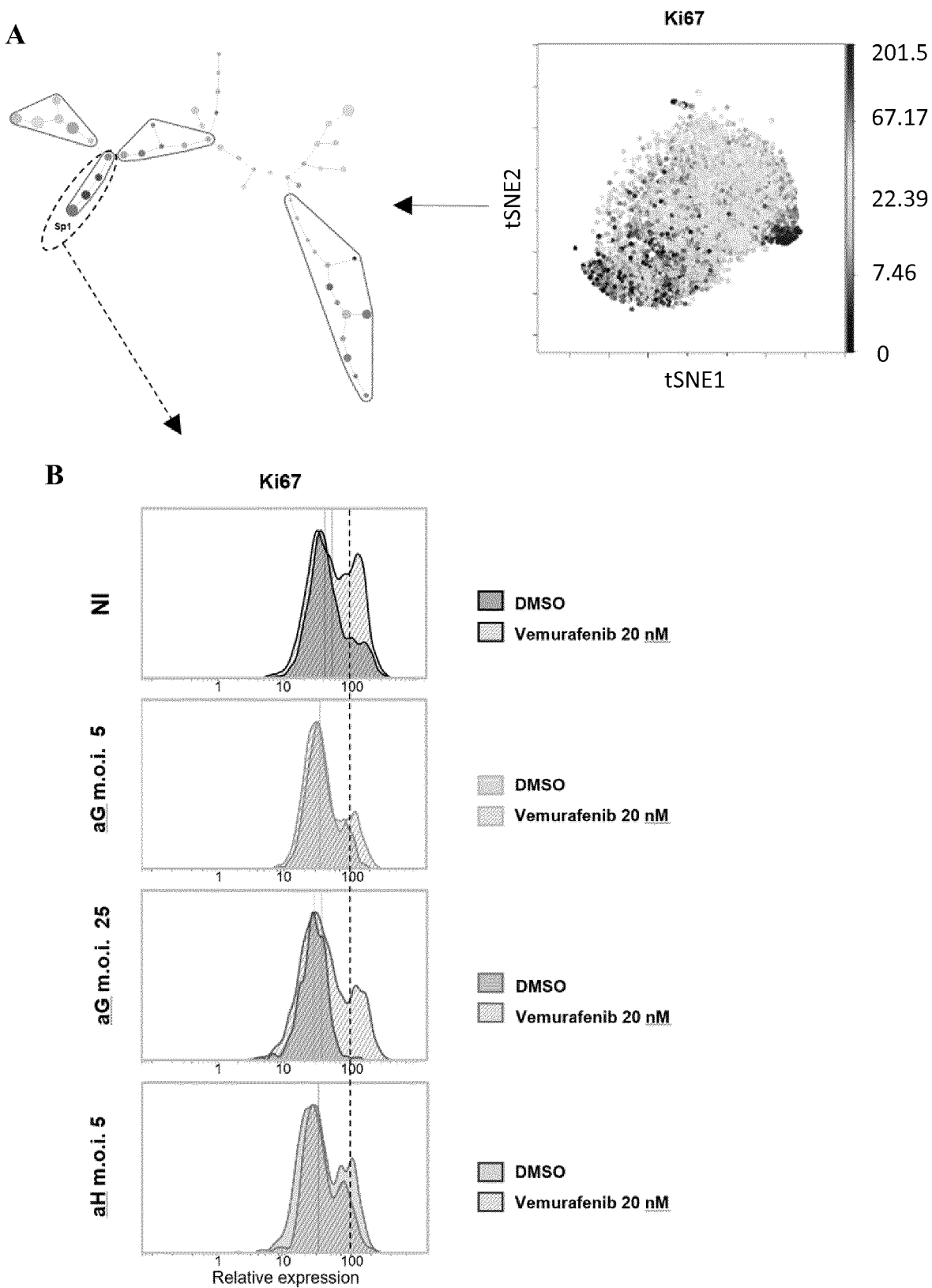
FIG. 4 shows single cell mass cytometry (viSNE and SPADE) analyses in various subpopulations within A375 cell line as described in Example 1. A: Analysis of the Ki67 proliferation marker shown for NI excipient-treated A375 cells. The grey scale line gives an indication of the fold change in Ki67 expression. On the right viSNE map from which the spanning-tree (shown on the left), is generated; B: Distribution of Ki67 expression for the Sp1 subpopulation selected in A for NI cells, aG cells (at m.o.i. 5 or 25) and aH cells (at m.o.i. 5), treated with vemurafenib (20 nM) or DMSO.

Single-cell mass cytometry analyses were conducted to identify various subpopulations within the A375 cell line. As an additional confirmation of the observed suppression of paradoxical proliferation, the expression of the proliferation marker Ki67 analyzed in the high Ki67 (fast-proliferating) subpopulation (Sp1), extracted from one of the conducted experiments, is shown in FIG. 4. In control cells, (NI and aG cells treated with 20 nM of vemurafenib (called hereafter as aGt, infected at m.o.i. 5 and at m.o.i. 25), Ki67 expression was higher than in similarly treated aH cells (called hereafter as aHt, infected at m.o.i. 5). Noteworthy, a slightly higher Ki67 expression was observed in excipient-treated (DMSO) aH cells (called hereafter as aHnt cells, infected at m.o.i. 5) compared with the excipient-treated aG cells (called hereafter as aGnt cells, infected at m.o.i. 5). Although not detected in the initial proliferation assay (FIG. 1C), a small vector-induced inhibitory effect is detectable in aG cells (at both m.o.i. values, compared with each other and to the NI cells). This inhibitory effect does not prevent the occurrence of paradoxical proliferation.

These results indicate that HuR overexpression can inhibit emergence of paradoxically proliferative subpopulations of A375 melanoma cells treated with low-dose vemurafenib. This suppression of paradoxical proliferation, in HuR overexpressing cells, is associated for a subset of cells, with an increased death rate, that occurs most likely in S phase of the cell cycle and with a G2/M accumulation.

Example 2: Effect of HuR Overexpression on the Subpopulation Size within the Heterogeneous Cell Response Mammalian cell lines, although often of clonal origin, are composed of heterogeneous cells both in terms of genetic expression (Lee et al., 2014, supra) and phenotypic behavior i.e. renewal capacity (Sato et al., 2016, supra). Based on such observations, it was tested whether the observed vemurafenib-induced paradoxical proliferation of A375 cells arises from cell heterogeneity, prompting an immediate adaptive response of a subset of cells to suboptimal vemurafenib exposure and whether HuR overexpression could preclude the occurrence of such an adaptive response.

In order to test this hypothesis, simultaneous analysis of various markers must be conducted at the level of a single cell (Fienberg et al., 2014, *Curr Top Microbiol Immunol*, 377:85-94). Although fluorescence-based flow cytometry allows the simultaneous analysis of up to 15 parameters, it is limited by the need to compensate for spectral overlap and the background due to cell autofluorescence, and may therefore lack sensitivity to detect small differences within an apparently homogenous cell population.

Therefore, single-cell mass cytometry was used (Di Palma et al., 2015, *Curr Opin Biotechnol*, 31:122-9) to detect discrete variations in the expression pattern of known markers either involved in the mechanism of reversible adaptive resistance to BRAF inhibitors: pERK1/2 (phospho-Extracellular Signal-Regulated Kinase1/2), pAKT (protein kinase B), epidermal growth factor receptor (EGFR), platelet-derived growth factor receptor-β (PDGFRB), phospho-eIF4E-binding protein 1 (p4EBP1) (Kazarian et al., 2010, supra; Sun et al., 2014, supra; Boussemart et al., 2014, supra), and/or in cell cycle control and functionally identified as HuR targets: cyclin B1, cyclin A, p53 (tumor protein p53), p21 (cyclin-dependent kinase inhibitor 1 or CDK-interacting protein 1), c-Myc (a regulator gene that codes for a transcription factor) (Wang et al., 2000, supra; Mazan-Mamczarz et al., 2003, *PNAS*, 100:8354-9; Wang at al., 2000, *EMBO J*, 19:2340-50; Lafon et al., 1998, *Oncogene*, 16:3413-21).

Ki67 was included as a marker of proliferation, cisPt194 (Cisplatin 194) was used to exclude dead cells (Fienberg et al., 2012, supra) and also to detect dying live cells. GFP was used as a quantitative sensitivity marker (FIG. 5B). Additionally, p53/p21 and pAKT/p4EBP1 pairs were also used to control for coupled variation within subpopulations (i.e. biologically coherent patterns).

Mass cytometry analysis was conducted as in Example 1. The following antibodies were used: $^{167}$Er-anti-pERK1/2 (T202/Y204) (clone D13.14.4E)/$^{152}$Sm-anti-pAKT (pS473) (clone D9E)/$^{149}$Sm-anti-p4EBP1 (T37/46) (clone 236B4)/$^{164}$Dy-anti-CyclinB1 (clone GNS-1)/$^{158}$Gd-anti-CyclinA (clone BF683)/$^{143}$Nd-anti-p53 (clone 7F5)/$^{159}$Tb-anti-p21/WAF1 (clone 12D1)/$^{176}$Yb-anti-cMyc (clone 9E10)/$^{169}$Tm-anti-GFP (clone 5F12.4). viSNE (visual interactive Stochastic Neighbor Embedding) maps and SPADE spanning-trees (a spanning-tree progression analysis of density-normalized events) were generated using 12 markers.

First, a viSNE analysis was performed on gated live singlets from samples enumerated below. viSNE maps high-dimensional data shown as a scatter plot (Van der Maaten, 2008, *Journal of Machine Learning Research*, 9:2579-605), in which each dot represents a cell and its position reflects the information from all the original dimensions i.e. the 12 markers shown in FIG. 7. Next, from each viSNE map, a spanning-tree progression analysis of density-normalized events (SPADE) was generated which uses a hierarchical clustering algorithm to generate a spanning-tree in an unsupervised manner. The target number of clusters to be reached was specified as 50. FIGS. 5 and 7 describe an experiment different from the one shown in FIG. 4. For the Ki67 marker (FIG. 5A1-A3), the viSNE maps for the NI and aG samples showed a very clear increase in the size of the high Ki67 subpopulation in the vemurafenib-treated (20 mM) (bottom) compared with the DMSO-treated cells (top) (FIG. 5A1-A3). The Ki67 spanning-trees for vemurafenib- and DMSO-treated NI cells and aGnt, aGt, aHnt and aHt cells are shown in FIG. 5A1-A3 (middle). Within them, based on the arborescence, four subsets were selected, potentially representing the spectrum of heterogeneity (Sp1, Sp2, Sp3 Sp4 subpopulations). Based on Ki67 expression levels, the selected subpopulations were defined as being fast-proliferating (Sp1), intermediary mild-proliferating (Sp2), slow-proliferating (Sp3) or as quiescent/slow-proliferating (Sp4, in which some of the clusters were Ki67 negative). In NI and aG cells, the size of Sp1 and Sp2 subpopulations were larger in the presence of vemurafenib than in its absence, contrary to aH cells, in which the size of these two subpopulations even appeared reduced under treatment (FIG. 5A1-A3, right pie-charts and FIG. 6). The size of the Sp4 quiescent/slow-proliferating subpopulation was larger in aHt cells than in aHnt cells but smaller in aGt cells than in aGnt cells.

Overall, these data confirm that HuR overexpression can overcome the increase in the proportion of the most rapidly proliferating (sp1, sp2) subpopulations that is induced upon suboptimal BRAF inhibition in the A375 cells and reduces the cell heterogeneous response (FIG. 6).

Example 3: Discriminating Sensitive from Emerging Resistant Cell Subpopulations

A more qualitative analysis of each of the four subpopulations defined in Example 2 (Sp1, Sp2, Sp3 and Sp4) was conducted, based on the expression profile of the 12 markers used to generate the viSNE maps.

Comparative expression distribution and median value comparisons are shown in FIG. 7. Lower Ki67 expression in aGt than in aGnt cells in Sp1 subpopulation clearly indicated that this fast-proliferating subpopulation is sensitive to low-dose vemurafenib treatment, whereas the Sp2 mild- and especially the Sp3 slow- and Sp4 quiescent/slow-proliferating subpopulations paradoxically proliferated under vemurafenib treatment.

In contrast, in aH cells, no such paradoxical proliferation was seen (this difference between aG and aH cells regarding the effects of vemurafenib treatment in mild/slow-proliferating subpopulations is hereafter called "HuR-specific pattern"). HuR overexpression alone (in DMSO-treated cells) induced a cytostatic effect in Sp1 subpopulation, but had a proliferative effect in the Sp4 quiescent/slow-proliferating subpopulation. This proliferative effect is equivalent to the one seen in Sp1 subpopulation in the experiment shown in FIG. 4. In FIG. 4, Sp1 subpopulation was defined as fast-proliferating, however the comparison of Ki67 expression range between the two experiments in aGnt cells, indicates that the proliferation rate of Sp1 cells in FIG. 4 experiment is equivalent to the one observed, in FIG. 7 experiment, in Sp2 or Sp3 cells. These differences related to variations in the overall cell proliferation rate between the two experiments, explain the variability seen in the proliferation assays in FIG. 2. The consequence is a difference in the hierarchical clustering and partitioning of cells. As an example, Sp1 subpopulation arborescence, in the spanning-tree shown in FIG. 5A, is slightly more developed than the one shown in FIG. 4.

pERK1/2 expression was lower as expected in aGt than in aGnt cells, in the Sp1 vemurafenib-responding subpopulation, but did not differentiate the subpopulations according to the HuR-specific pattern. Instead, there was an even higher expression level of pERK1/2 in aHt than in aHnt cells (as in aG cells) in the Sp2 and Sp3 subpopulations. This observation is indicating that the MAPK pathway activation is not prevented by HuR overexpression but even maintained (comparatively for example to PI3K/AKT), which might explain the more homogeneous response to BRAF inhibition.

As expected, pAKT and p4EBP1 followed each other pattern across the samples (biologically coherent patterns). Importantly, pAKT in Sp3 subpopulation and p4EBP1 in Sp2 and Sp3 subpopulations, did follow the HuR-specific pattern, so did PDGFRB in Sp3 subpopulation. Therefore, HuR induced suppression of paradoxical proliferation (Ki67 expression) was associated with similarly reduced pattern responses of pAKT in the slow-proliferating Sp3 subpopulation, of p4EBP1 in the mild-(Sp2) and slow- (Sp3) proliferating subpopulations and of PDGFRB in the slow-proliferating Sp3 subpopulation.

This patterns corroborates previous studies showing that expression levels of pAKT and its downstream target p4EBP1 discriminate sensitive from adaptive/resistant melanoma cell lines, better than pERK1/2 expression levels (Nazarian et al., 2010, Nature, 468:973-7), and is consistent with the notion that overexpressed PDGFRB is involved in the mechanisms of adaptive resistance in melanoma.

Contrary to PDGFRB, EGFR did not follow the HuR-specific pattern in any of the subpopulations, but in Sp3 and Sp4 quiescent/slow-proliferating cells, aGnt cells showed a higher EGFR expression level than aHnt cells in which an increased proliferation rate was induced. Consistent with this observation, previous studies have shown that A375 cells engineered to express EGFR proliferate slower and are more likely to become resistant to BRAF inhibitors (Sun et al., 2014, Nature, 508:118-22).

The fact that HuR overexpression differentially affected various subpopulations within the same melanoma cell line and that this effect depended at least in part on the proliferation rate of these subpopulations (suppression of the paradoxical proliferation in slower-proliferating cells) may be linked to the proliferative effect of HuR on these subpopulations. Slow-proliferating cells are often considered to be the pool of cells giving rise to drug resistance in various malignancies and in particular in melanoma where resistant cell lines tend to have a slower doubling-times compared with sensitive cell lines (Søndergaard et al., 2010, J. Transl. Med., 8:39).

Regarding markers directly involved in cell cycle regulation and/or functionally characterized as HuR targets: Cyclin B1, could differentiate the Sp2 and Sp3 subpopulations according to the HuR-specific pattern. This was not the case for Cyclin A which may be due, considering that S phase contains a large fraction of Cyclin A expressing cells, to the reduced number of cells in the S phase observed for aHt cells (FIG. 3B). Regarding p53 and p21, their expression pattern appeared as expected synchronized in the Sp1 and Sp2 subpopulations (biologically coherent patterns) in which, in contrast to other markers (Ki67, pERK1/2, Cyclin B1), a right tail of higher expression was clearly maintained in aHt compared with aGt cells. This pattern means that, under vemurafenib treatment, the higher HuR expression allows these two targets to be better expressed in the fast and mild-proliferating cells in which a potentially more efficient cytostatic or cytotoxic effect is expected to occur. Indeed, in addition to the more efficient cytostatic effect of vemurafenib indicated by Ki67 staining in Sp2 subpopulation, cisPt194 staining (FIG. 7, last marker), which indicates the death tendency, was higher in aHt cells in Sp1 and Sp2 subpopulations compared with aGt cells. This observation is consistent with the above described size reduction of these two subpopulations in aH-treated cells (FIG. 5A1-A3, FIG. 6). Therefore, in the fast-proliferating vemurafenib-sensitive and the mild-proliferating treated cells, HuR overexpression was associated with increased expression of p53 and p21, increased vemurafenib-induced death tendency and a reduction in population size.

Overall, the observed expression profile of the subset of cells that paradoxically proliferate, mimics some of the expression traits described among the mechanisms of adaptive resistance to BRAF inhibition and is therefore relevant for the characterization of early development of an adaptive resistance in BRAF-mutated cancers under treatment with BRAF inhibitors.

Therefore, altogether, those data support that HuR overexpression can prevent the immediate heterogeneous response to low-dose BRAF inhibition and the subsequent paradoxical proliferation that occurs in some subpopulations of melanoma cells and that the use of HuR overexpression inducers may be a useful tool to avoid the emergence of adaptive resistant cells to BRAF inhibitors.

Example 4: Screening of Compounds that Increase Cellular Expression of HuR

Agents that have been shown to increase HuR cytoplasmic localization are tested for their ability to have similar effects on melanoma cell lines as the one obtained with the adenovirus. Cell lines. Experiments are conducted on the A375 and the MALME-3M cells (melanoma BRAF mutated sensitive cell lines) and also on non-melanoma BRAF mutated cells like for example the HT-29 colon carcinoma derived cells.

Compounds.

Agents such as the PPARδ/β receptor agonist GW501516, lithium salts (e.g. LiCl) and estrogen receptor antagonists are tested.

Cell proliferation assay and Western blot analysis were conducted as described in Example 1. Mass cytometry analysis as described in Examples 2 and 3.

The melanoma cell lines are exposed to different concentrations of above agents and their nuclear and cytoplasmic HuR content are compared to excipient treated cells using western blot analysis. The lowest efficient concentration of the agent capable of increasing HuR cytoplasmic content of melanoma cells, which does not affect their proliferation rate is determined (similarly to what has been done in the adenovirus-mediated experiments in Example 1). The selected compounds (and concentrations) are checked for their ability to mimic the adenovirus-mediated effects observed in the A375 cells i.e. the suppression of paradoxical proliferation assessed in proliferation assays. Classical methods such as siRNA-mediated knockdown of HuR are used to demonstrate that the effects of the agents are HuR-mediated or alternatively, when available, selective potent receptor inhibitors are used to check if the effects of agonists are mediated by their receptors (applicable to PPARδ/β receptor agonists). Finally, experiments are conducted to check if agent(s) capable of increasing HuR cell expression and in particular cytoplasmic content, can prevent the occurrence of resistance upon chronic vemurafenib exposure. A375 or MALME-3M cells are exposed to incremental dose of vemurafenib combined with either an agent capable of increasing HuR cell expression and in particular cytoplasmic expression or its excipient alone over a period of two month during which the sensitivity to vemurafenib is monitored using proliferation assays. These experiments are also monitored with mass cytometry expression analysis of selected markers in order to characterize the maintenance or suppression of the heterogeneous response to vemurafenib treatment.

Example 5: Comparative Examples not Inducing an Increase Cellular Expression of HuR Some HIV protease inhibitors (such as Nelfinavir) have been used in combination with a BRAF inhibitor to potentiate its effect (Smith et al., 2016, cancer cell, 29(3): 270-284) and some HIV protease inhibitors have (such as Lopinavir) been reported as increasing the cytosolic translocation of HuR (Chen et al., 2009, Biochem Pharmacol., 78(1): 70-77). Further, some polyamine depleting agents i.e. agents reducing the cellular content in polyamines ($\alpha$-difluoromethylornithine (DFMO), also named Eflornithin) have been reported to modulate cytoplasmic HuR levels (Zou et al., 2006, J. Biol. Chem., 281(28):19387-94). Therefore, a polyamine, Eflornithine (DFMO) and a HIV protease inhibitor, lopinavir ((2S)-N-[(2S,4S,5S)-5-[[2-(2,6-dimethylphenoxy)acetyl]amino]-4-hydroxy-1,6-diphenylhexan-2-yl]-3-methyl-2-(2-oxo-1,3-diazinan-1-yl)butanamide) were tested as comparative examples ((comparative compounds C1 and C2, respectively)) for their ability to increase HuR cytoplasmic localization in melanoma (A375 and the MALME-3M cells (melanoma BRAF mutated sensitive cell lines) cell lines as follows and analysis was conducted by Western blot analysis as described in Example 1 [, except that the cells were treated with comparative compound C1 dissolved in DMSO at 5 mM or at 1 mM for 6 consecutive days, where fresh medium with C1 was added in 6 well plates every day and the cells were split every 3 days or the cells were treated with C2 at 15 µM dissolved in DMSO for 24 h. Cell fractionation was conducted using the NE-PER Nuclear and Cytoplasmic Extraction Reagents (Thermo-Fisher Scientific) according to the manufacturer's instructions. Nuclear (N) and cytoplasmic (C) fractions were analyzed for HuR expression by western blot as described above. Anti-$\alpha$-tubulin mouse monoclonal antibody (Clone B-5-1-2, 1:10000/Sigma Aldrich) and anti-lamin A mouse monoclonal antibody (Santa-Cruz/4A58-sc-7148, 1:500) were used as a control to check the quality of the cell fractionation. As a comparison of successful increase in HuR cytoplasmic content, western blot analysis was performed on cells infected with aG or aH at m.o.i 5, 25 or 125 as described in Example1 (FIG. 8C).

Western blot analysis shows that no increase of HuR cytoplasmic content occurred in both cancer cells upon exposure to C1 (FIG. 8A1-2) and C2 (FIG. 8B1-2). As a comparison, successful increase in HuR cytoplasmic content was observed in aH infected cells compared to control aG infected cells (FIG. 1A and FIG. 8C).

These data support that comparative compounds do not enhance the cytoplasmic expression of HuR in the present assay. Therefore, in order to identify HuR/ELAV protein enhancers of the invention, it is important to assess their ability to enhance the cytoplasmic expression of HuR as described herein or in a screening assay according to the invention.

Example 6: Lithium Potentiation of Vemurafenib

Lithium Chloride (LiCl) was tested for its ability to increase HuR cytoplasmic localization in melanoma cell lines and therefore to enhance the effect of vemurafenib (PLX4032) on melanoma cell lines (described in Example 5).

Western blot analysis was conducted as described in Examples 1 and 5, except that cells were treated with LiCl at 1 mM (for 6 h for A375 and for 24 h for MALME-3M cells) before cell lysis and analysis. As seen on FIG. 9A, tubulin was detected in the nuclear fraction (N), indicating a slight contamination of the N fraction by the cytoplasmic fraction (C), but no contamination of the C fraction by the N fraction was observed (no lamin A detected in the cytoplasm). Considering that HuR is mainly a nuclear protein, the absence of any nuclear contamination in the cytoplasm as observed here fulfils the experimental requirements. The increased cytoplasmic expression of HuR was quantified as being respectively 80% and 50% increased in A375 and Malme 3M melanoma cells using an image quantification software (ImageJ).

siRNA-Mediated Knockdown of HuR:

MALME-3M cells were seeded at 700'000 cells per well in six-well tissue culture plates and transfected the next morning with either 50 nM of a mixture of small interfering RNA (siRNA) targeting HuR i.e., HuR-siRNA-duplexes from Santa Cruz (Dallas, Tex., USA, siRNA-HuR, sc-35619) and Flexitube (siRNAs for HuR, SI03246887, SI03246551, SI00300139, Qiagen, Netherlands) or the same amount of a non-targeting siRNA from Santa Cruz (Ctl-siRNA, sc-36869, Fluorescein conjugated) (control, ctrl-siRNA). The transfections were performed using Santa Cruz transfection reagents according to the manufacturer's instructions. The expression of HuR in transfected cells was assessed in western blot analysis as described above.

Cell proliferation was conducted as described in Example 1, except that MALME-3M cells transfected with siRNA-HuR or ctrl-siRNA were transferred from six well plates at 10'000 cells per well in 96-well tissue culture plates (100 µl medium) and after 24 h the cells were treated with vemurafenib for 48 h at 31.25 nM, 125 nM, 250 nM, 500 nM, 1000 nM and 4000 nM or with vemurafenib and LiCl (1 mM) in quadruplicate (FIG. 9C). Cell proliferation is expressed as a percentage of the absorbance compared with the DMSO-treated cells.

Western blot analysis shows an increase of both total amount of HuR expression and HuR cytoplasmic content that occurs in both cancer cells upon exposure to LiCl (FIG. 9A). In those cells, Li treatment clearly increases the total amount of HuR expression with a dose effect visible on both endogenous HuR and exogenous epitope-tagged HuR (visible as an extra band appearing above endogenous HuR). Note that an almost maximum effect is detectable at low concentration (1 mM) (FIG. 9A$_3$). MALME-3M cells transfected with the HuR-siRNA shows a decreased expression of nuclear (N) and cytoplasmic (C) HuR, compared to cell transfected with the ctrl-siRNA, supporting that silencing of HuR (e.g. with siRNA) was effective in this assay (FIG. 9B).

In MALME-3M cells transfected with ctrl-siRNA, i.e. cells with normal HuR expression, the group treated with a combination LiCl and vemurafenib-had a lower rate of proliferation as compared to the control Licl non-pretreated cells (FIG. 9C1), whereas silencing HuR in those cells resulted in the abolition of the difference in proliferation between the control group and the group treated with a combination LiCl and vemurafenib- (FIG. 9C2).

These data support that Li enhances both the total amount of HuR expression and the cytoplasmic expression of HuR and it potentiates the effect of a BRAF inhibitor in decreasing cancer cell proliferation. The abolition of this enhancing effect by knocking down HuR supports a HuR-mediated effect of LiCl.

The invention claimed is:

1. A method for treating a BRAF-mutated cancer in a patient suffering therefrom, said method comprising the administration of a therapeutically effective amount of at least one enhancer of HuR/ELAV protein or a pharmaceutically acceptable formulation thereof, to a patient in need of treatment, wherein said at least one enhancer of HuR/ELAV protein or any suitable pharmaceutically acceptable formulation thereof is to be administered in combination with at least one BRAF inhibitor.

2. The method according to claim 1, wherein said enhancer of HuR/ELAV protein is an enhancer of the expression of HuR/ELAV protein.

3. The method according to claim 1, wherein said at least one BRAF inhibitor is selected from vemurafenib or a precursor thereof, encorafenib, GDC0879, CEP-32496 and dabrafenib or a mixture of at least two of those.

4. The method according to claim 1, wherein said at least one BRAF inhibitor is vemurafenib or a precursor thereof.

5. The method according to claim 1, wherein said enhancer of HuR/ELAV protein is selected from a selective estrogen-receptor modulator, a PPARβ or δ agonist and lithium (Li) or salts thereof.

6. The method according to claim 1, wherein said BRAF-mutated cancer is a BRAF V600 mutated cancer.

7. The method according to claim 1, wherein said BRAF-mutated cancer is a BRAF mutated melanoma.

8. The method according to claim 1, wherein said BRAF-mutated cancer is a BRAF mutated papillary thyroid cancer (PTC).

9. The method according to claim 1, wherein said BRAF-mutated cancer is a BRAF mutated colorectal carcinoma (CRC).

10. The method according to claim 1, wherein said BRAF-mutated cancer is selected from BRAF mutated papillary craniopharyngioma, classical hairy-cell leukaemia (HCL-C) metanephric kidney adenoma, a BRAF-mutated lung cancer, a BRAF mutated ovarian cancer, glioma, ependymoma, non-Hodgkin lymphoma, liver, stomach or esophageal cancer.

11. The method according to claim 1, wherein the enhancer of HuR/ELAV protein is lithium (Li) or a salt thereof.

12. A method of prevention of the emerging of adaptive BRAF therapy resistance comprising the administration of a therapeutically effective amount of at least one enhancer of HuR/ELAV protein or any suitable pharmaceutically acceptable formulation thereof, in a subject suffering from a BRAF mutated solid tumor cancer, wherein said at least one enhancer of HuR/ELAV protein or any suitable pharmaceutically acceptable formulation thereof is to be administered in combination with at least one BRAF inhibitor.

13. A pharmaceutical composition comprising at least one enhancer of HuR/ELAV protein and at least one BRAF inhibitor and at least one pharmaceutically acceptable carrier.

14. The pharmaceutical composition according to claim 13, wherein said at least one BRAF inhibitor is vemurafenib or a precursor thereof.

15. The pharmaceutical composition according to claim 13, wherein the enhancer of HuR/ELAV protein is lithium (Li) or a salt thereof.

16. A method of identifying agents useful in the potentiation of therapeutic effects of BRAF inhibitors, said method comprising the steps of:
   a) providing isolated mutated cancer cells;
   b) contacting said candidate agent with said mutated cancer cells in combination with a BRAF inhibitor; and
   c) determining the ability of the said agent to increase HuR cell expression and/or cytoplasmic content of the cancer cells without affecting their proliferation rate compared to HuR cell expression and/or cytoplasmic content in absence of said agent; wherein the ability of an agent to increase HuR cell expression and/or cytoplasmic content of the cancer cells is indicative of an agent that is capable of suppressing paradoxical proliferation in cancer cells in combination with a BRAF inhibitor; and/or
   c') when said cells are capable of generating a paradoxical proliferation response in presence of a BRAF inhibitor and in absence of agent, determining the ability of said agent, when contacted under step b) at a concentration where HuR cell expression and/or cytoplasmic content of the cancer cells is increased without affecting substantially their proliferation rate, to suppress paradoxical proliferation in said cells compared to control in combination with a BRAF inhibitor alone; wherein the ability of an agent to suppress paradoxical proliferation is indicative of an agent that is capable of preventing the arising of resistance to BRAF inhibitor administration.

17. The method according to claim 16, wherein steps c and c' are conducted.

18. The method according to claim 16, wherein step c') is carried out by determining the ability of said agent, combined with a BRAF inhibitor, to suppress paradoxical proliferation in said mutated cancer cells capable of generating a paradoxical proliferation response in presence of a BRAF inhibitor and in absence of agent, where those cells are infected with an adenovirus overexpressing a control protein as compared to the same cells infected with an HuR overexpressing adenovirus contacted with a BRAF inhibitor alone.

* * * * *